(12) United States Patent
Kikuchi et al.

(10) Patent No.: US 8,779,140 B2
(45) Date of Patent: Jul. 15, 2014

(54) CRYSTAL OF FUSED PYRIDINE COMPOUND SALT

(75) Inventors: Takashi Kikuchi, Tokyo (JP); Katsuhiko Gato, Tokyo (JP); Koichiro Mukoyoshi, Tokyo (JP); Tsuyoshi Kitamura, Tokyo (JP); Takeshi Kawakami, Tokyo (JP); Hironobu Yasuda, Ibaraki (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 13/806,909

(22) PCT Filed: Jun. 22, 2011

(86) PCT No.: PCT/JP2011/064291
§ 371 (c)(1),
(2), (4) Date: Dec. 26, 2012

(87) PCT Pub. No.: WO2011/162300
PCT Pub. Date: Dec. 29, 2011

(65) Prior Publication Data
US 2013/0102628 A1    Apr. 25, 2013

(30) Foreign Application Priority Data
Jun. 23, 2010    (JP) .................................. 2010-143226

(51) Int. Cl.
*C07D 471/04*    (2006.01)

(52) U.S. Cl.
USPC ........................................................ 546/113

(58) Field of Classification Search
None
See application file for complete search history.

(56) References Cited

U.S. PATENT DOCUMENTS

| 2009/0270376 A1 | 10/2009 | Inoue et al. |
| 2011/0039822 A1 | 2/2011 | Inoue et al. |

FOREIGN PATENT DOCUMENTS

| JP | WO2007/077949 | * | 7/2007 | .......... C07D 471/04 |
| JP | 2009-522206 | | 6/2009 | |
| JP | WO2007/077949 | * | 7/2013 | .......... C07D 471/04 |
| WO | WO 2007/077949 A1 | | 7/2007 | |

OTHER PUBLICATIONS

Bastin et al. In Organic Process Research & Development 2000, 4, 427-435.*
Morissette et al. in Advanced Drug Delivery Reviews, 56, 275-300 (2004).*
Sheth et al. in KONA, 23, 36-48 (2005).*
International Search Report issued Sep. 6, 2011 in Application No. PCT/JP2011/064291.
International Preliminary Report on Patentability & Written Opinion issued Jan. 15, 2013 in Application No. PCT/JP2011/064291.
Edited by C.G. Wermuth, the Practice of Medicinal Chemistry (Last volume Technomics, Inc., Issued Sep. 25, 1999, pp. 347-365 (With Partial English Translation).
Written and Edited by Teisuke Okano, Shin-Yakuzaigaku Soron (3$^{rd}$ revision), Nankodo Co. Ltd., Apr. 10, 1987, pp. 110, 111, 257 and 258 (With Partial English Translation).

* cited by examiner

*Primary Examiner* — Dennis Heyer
(74) *Attorney, Agent, or Firm* — Oblon, Spivak, McClelland, Maier & Neustadt, L.L.P.

(57) ABSTRACT

[Problem]
A salt or crystal of a compound which is highly stable in a solid state and useful as a bulk material for the preparation of a pharmaceutical product is provided.
[Means for Solution]
4-{[(1R,2s,3S,5s,7s)-5-Hydroxy-2-adamantyl]amino}-1H-pyrrolo[2,3-b]pyridine-5-carboxamide succinate, 4-{[(1R,2s,3S,5s,7s)-5-hydroxy-2-adamantyl]amino}-1H-pyrrolo[2,3-b]pyridine-5-carboxamide hydrobromide, and 4-{[(1R,2s,3S,5s,7s)-5-hydroxy-2-adamantyl]amino}-1H-pyrrolo[2,3-b]pyridine-5-carboxamide hydrochloride and crystals thereof are useful as a bulk material for the preparation of a solid preparation, in particular, a solid dispersion preparation. Furthermore, the crystal of the hydrobromide has excellent stability in a solid state and is useful as a bulk material for the preparation of a pharmaceutical product.

7 Claims, 19 Drawing Sheets

CRYSTAL OF FUSED PYRIDINE COMPOUND SALT

TECHNICAL FIELD

The present invention relates to a salt and/or crystal of 4-{[(1R,2s,3S,5s,7s)-5-hydroxy-2-adamantyl]amino}-1H-pyrrolo[2,3-b]pyridine-5-carboxamide, which is useful as a bulk material for the preparation of a pharmaceutical product.

BACKGROUND ART

A fused heterocyclic compound and a salt thereof, which have an excellent JAK3 inhibitory activity, and are thus useful as an agent for treating and/or preventing diseases caused by undesirable cytokine signal transduction (for example, rejection during live-donor transplantation, rheumatism, psoriasis, autoimmune diseases, asthma, atopic dermatitis, Alzheimer's disease, and atherosclerotic disease, etc.), or diseases caused by abnormal cytokine signal transduction (for example, cancer and leukemia, etc.), are described in Patent Document 1. Among these, 4-{[(1R,2s,3S,5s,7s)-5-hydroxy-2-adamantyl]amino}-1H-pyrrolo[2,3-b]pyridine-5-carboxamide represented by the following formula (I), as disclosed in Example compound Ex. 121, is a compound which exhibits an excellent activity and is expected to act particularly as an agent for inhibiting rejection reaction during organ/tissue transplantation or for treating rheumatism, psoriasis, or the like.

[Chem. 1]

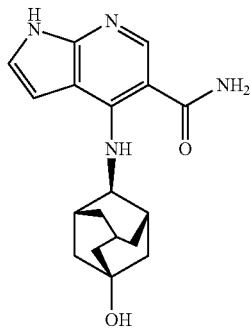

(I)

The solid stability of a compound to be a development candidate of a pharmaceutical is an important factor in industrial operations as well as maintenance of quality. For the stability of a drug substance itself, it is necessary to evaluate the stability of quality required to maintain the efficacy and the safety of pharmaceutical products, and to obtain information required to determine the storage methods and the shelf life for pharmaceutical products. Therefore, a stability test is considered as one of the most important tests for the preparation of pharmaceutical products (Thermal Measurement, 2004, 31(2), pp. 80-86).

In Patent Document 1, a free form of the compound of the formula (I) is disclosed, but a crystal of the compound is not disclosed. There is a demand for a bulk material for the preparation of a pharmaceutical product, which is suitable for formulation and is physicochemically stable in terms of quality assurance.

RELATED ART

Patent Document

Patent Document 1: Pamphlet of International Publication WO 2007/077949

DISCLOSURE OF INVENTION

Problems to be Solved by the Invention

A salt and/or crystal of 4-{[(1R,2s,3S,5s,7s)-5-hydroxy-2-adamantyl]amino}-1H-pyrrolo[2,3-b]pyridine-5-carboxamide having solid stability which is suitable as a bulk material for the preparation of a pharmaceutical product, and a solid preparation including the same are provided.

Means for Solving the Problems

The present inventors have performed extensive studies to obtain a solid having stability and solubility suitable as a bulk material of a pharmaceutical with a compound of the formula (I). They have made attempts to prepare many salts, specifically hydrochloride, hydrobromide, sulfate, mesylate, tosylate, phosphate, succinate, L-tartrate, fumarate, and L-maleate, in addition to crystal samples of free forms, and have further investigated the crystallization conditions, and as a result, they have prepared a number of crystal forms, including crystal polymorphs. However, it was difficult to find a salt and/or a crystal having both physicochemical stability and solubility compatible with the estimated clinical dose. Accordingly, the present inventors have tried to improve the solubility by formulating the compound of the formula (I) into a preparation in the form of a solid dispersion, and have further searched for a crystal form with an index of solubility in an organic solvent used for a solid dispersion, specifically hydrated EtOH. As a result, they have only found that the crystals of succinate, hydrobromide, and hydrochloride each have solubility suitable for a solid dispersion preparation. As a result of further search, they have found that a crystal of hydrobromide has excellent storage stability in a solid state and has properties suitable as a bulk material for the preparation of a pharmaceutical product.

Specifically, the present invention relates to a solid preparation including a solid selected from 4-{[(1R,2s,3S,5s,7s)-5-hydroxy-2-adamantyl]amino}-1H-pyrrolo[2,3-b]pyridine-5-carboxamide succinate, 4-{[(1R,2s,3S,5s,7s)-5-hydroxy-2-adamantyl]amino}-1H-pyrrolo[2,3-b]pyridine-5-carboxamide hydrobromide, and 4-{[(1R,2s,3S,5s,7s)-5-hydroxy-2-adamantyl]amino}-1H-pyrrolo[2,3-b]pyridine-5-carboxamide hydrochloride, or crystals thereof, and a pharmaceutically acceptable carrier. In a certain embodiment, the solid preparation is a solid preparation including hydrobromide and a pharmaceutically acceptable carrier, and in another embodiment, a solid preparation of a hydrobromide crystal and a pharmaceutically acceptable carrier. In addition, in a certain embodiment, the solid preparation is a solid preparation including a solid dispersion obtained by dissolving 4-{[(1R,2s,3S,5s,7s)-5-hydroxy-2-adamantyl]amino}-1H-pyrrolo[2,3-b]pyridine-5-carboxamide succinate, 4-{[(1R,2s,3S,5s,7s)-5-hydroxy-2-adamantyl]amino}-1H-pyrrolo[2,3-b]pyridine-5-carboxamide hydrobromide, and 4-{[(1R,2s,3S,5s,7s)-5-hydroxy-2-adamantyl]amino}-1H-pyrrolo[2,3-b]pyridine-5-carboxamide hydrochloride, and crystals thereof, and a pharmaceutically acceptable, water-soluble polymeric carrier in a co-solvent, and then drying. In another embodiment, the solid preparation is a solid preparation including a solid dispersion containing any one of 4-{[(1R,2s,3S,5s,7s)-5-hydroxy-2-adamantyl]amino}-1H-pyrrolo[2,3-b]pyridine-5-carboxamide succinate, 4-{[(1R,2s,3S,5s,7s)-5-hydroxy-2-adamantyl}-1H-pyrrolo[2,3-b]pyridine-5-carboxamide hydrobromide, or 4-{[(1R,2s,3S,5s,7s)-5-hydroxy-2-adamantyl]amino}-1H-pyrrolo[2,3-b]pyridine-5-carboxamide hydrochloride.

Furthermore, the present invention relates to a crystal of 4-{[(1R,2s,3S,5s,7s)-5-hydroxy-2-adamantyl]amino}-1H-pyrrolo[2,3-b]pyridine-5-carboxamide hydrobromide, which has properties suitable as a bulk material for the preparation of a pharmaceutical product. Particularly, the present invention relates to Form B45, Form A87, Form A61, and Form A36 crystals having excellent stability in a solid state, and in particular, a Form B45 crystal which is most stable. The present invention further relates to a crystal (Form A24) of 4-{[(1R,2s,3S,5s,7s)-5-hydroxy-2-adamantyl]amino}-1H-pyrrolo[2,3-b]pyridine-5-carboxamide succinate and crystals (Form A33 and Form A34) of 4-{[(1R,2s,3S,5s,7s)-5-hydroxy-2-adamantyl]amino}-1H-pyrrolo[2,3-b]pyridine-5-carboxamide hydrochloride.

That is, the following polymorphs exist as the hydrobromide of the present invention, and the present invention encompasses such individual crystal polymorphs.

[A] Form B45 Crystals: Crystals having characteristic peaks of powder X-ray diffraction shown at angles 2θ (°) of about 9.0, 17.6, 18.1, 18.3, 23.0, and 27.3; and in a certain embodiment, crystals having a starting melting temperature at around 315° C. in TG/DTA analysis.

[B] Form A87 Crystals: Crystals having characteristic peaks of powder X-ray diffraction shown at angles 2θ (°) of about 8.3, 13.4, 18.3, 19.3, 20.8, 25.1, and 28.6; and in a certain embodiment, crystals having a starting melting temperature at around 319° C. in TG/DTA analysis.

[C] Form A61 Crystals: Crystals having characteristic peaks of powder X-ray diffraction shown at angles 2θ (°) of about 7.3, 13.8, 16.8, 18.4, 20.9, and 21.9; and in a certain embodiment, crystals having a starting melting temperature at around 319° C. in TG/DTA analysis.

[D] Form A36 Crystals: Crystals having characteristic peaks of powder X-ray diffraction shown at angles 2θ (°) of about 8.9, 16.6, 17.9, 18.7, 21.3, and 23.8; and in a certain embodiment, crystals having a starting melting temperature at around 312° C. in TG/DTA analysis.

[E] Form B11 Crystals: Crystals having characteristic peaks of powder X-ray diffraction shown at angles 2θ (°) of about 7.8, 12.8, 16.4, 17.1, 18.3, 24.7, 25.3, and 25.8; and in a certain embodiment, crystals having a water of crystallization-eliminating temperatures at around 111° C. and starting melting temperatures at around 315° C. in TG/DTA analysis.

[F] Form B21 Crystals: Crystals having characteristic peaks of powder X-ray diffraction shown at angles 2θ (°) of about 15.7, 17.5, 19.5, 20.5, 23.0, 23.7, and 27.0; and in a certain embodiment, crystals having water of crystallization eliminating temperatures at around 82° C. and starting melting temperatures at around 318° C. in TG/DTA analysis.

The present invention further includes the following crystals of 4-{[(1R,2s,3S,5s,7s)-5-hydroxy-2-adamantyl]amino}-1H-pyrrolo[2,3-b]pyridine-5-carboxamide succinate, and crystals of 4-{[(1R,2s,3S,5s,7s)-5-hydroxy-2-adamantyl]amino}-1H-pyrrolo[2,3-b]pyridine-5-carboxamide hydrochloride.

[G] Form A24 Crystals of Succinate: Crystals having characteristic peaks of powder X-ray diffraction shown at angles 2θ (°) of about 7.1, 12.8, 17.1, 17.6, and 24.3; and in a certain embodiment, crystals having a starting melting temperature at around 215° C. in TG/DTA analysis.

[H] Form A33 Crystals of Hydrochloride: Crystals having characteristic peaks of powder X-ray diffraction shown at angles 2θ (°) of about 8.7, 15.1, 16.8, 17.5, 19.9, 24.6, and 26.2; and in a certain embodiment, crystals having a starting melting temperature at around 270° C. in the TG/DTA analysis.

[I] Form A34 Crystals of Hydrochloride: Crystals having characteristic peaks of powder X-ray diffraction shown at angles 2θ (°) of about 7.9, 13.0, 13.4, 16.6, 17.1, and 25.4; and in a certain embodiment, crystals having water of crystallization eliminating temperatures at around 110° C. in TG/DTA analysis.

Furthermore, the term "about" in the characteristic peaks of powder X-ray diffraction shown at angles 2θ denotes ±0.2°, in another embodiment, ±0.1°. Each crystal can be characterized by a powder X-ray diffraction spectrum, but with the powder X-ray diffraction, crystal lattice intervals and overall patterns are important for identification of crystals in terms of the properties of the data, and since the relative intensity may vary slightly depending on the direction of crystal growth, the particle size, and the measurement conditions, it should not be strictly construed.

In addition, in the starting melting temperature in the thermal analysis, the term "around" means ±2° C., and in another embodiment, ±1° C. For example, the starting melting temperature of the Form B45 crystal means around 315° C., that is, 313 to 317° C. The respective crystals can be characterized in the results of each thermal analysis, but since the conclusion may vary slightly depending on the measurement instrument, the rate of temperature increase, or the data analysis, it should not be strictly construed.

Moreover, the present invention relates to (1) a pharmaceutical composition including any crystals of [A] to [I] as described above, as an active ingredient; (2) the pharmaceutical composition as described in (1), which is a pharmaceutical composition for treating rejection during live-donor transplantation, rheumatism, and/or psoriasis; (3) use of any crystals of [A] to [I] as described above for the preparation of a pharmaceutical composition for treating rejection during live-donor transplantation, rheumatism, and/or psoriasis; (4) a method for treating rejection during live-donor transplantation, rheumatism, and/or psoriasis, including administrating an effective amount of any crystals of [A] to [I] as described above to a patient; (5) any crystals of [A] to [I] as described above for treating rejection during live-donor transplantation, rheumatism, and/or psoriasis; and (6) use of any crystals of [A] to [I] as described above for treating rejection during live-donor transplantation, rheumatism, and/or psoriasis.

Effects of the Invention

4-{[(1R,2s,3S,5s,7s)-5-Hydroxy-2-adamantyl]amino}-1H-pyrrolo[2,3-b]pyridine-5-carboxamide succinate, 4-{[(1R,2s,3S,5s,7s)-5-hydroxy-2-adamantyl]amino}-1H-pyrrolo[2,3-b]pyridine-5-carboxamide hydrobromide, and 4-{[(1R,2s,3S,5s,7s)-5-hydroxy-2-adamantyl]amino}-1H-pyrrolo[2,3-b]pyridine-5-carboxamide hydrochloride and crystals thereof of the present invention have solubility suitable for a solvent for a solid dispersion, and are useful as a bulk material for the preparation of a solid preparation, in particular, a solid dispersion preparation.

Furthermore, the crystal of 4-{[(1R,2s,3S,5s,7s)-5-hydroxy-2-adamantyl]amino}-1H-pyrrolo[2,3-b]pyridine-5-carboxamide hydrobromide of the present invention has excellent stability in a solid state, and in particular, the Form B45 crystal is useful as a bulk material for the preparation of a pharmaceutical product.

EMBODIMENTS FOR CARRYING OUT THE INVENTION

Figure 1:
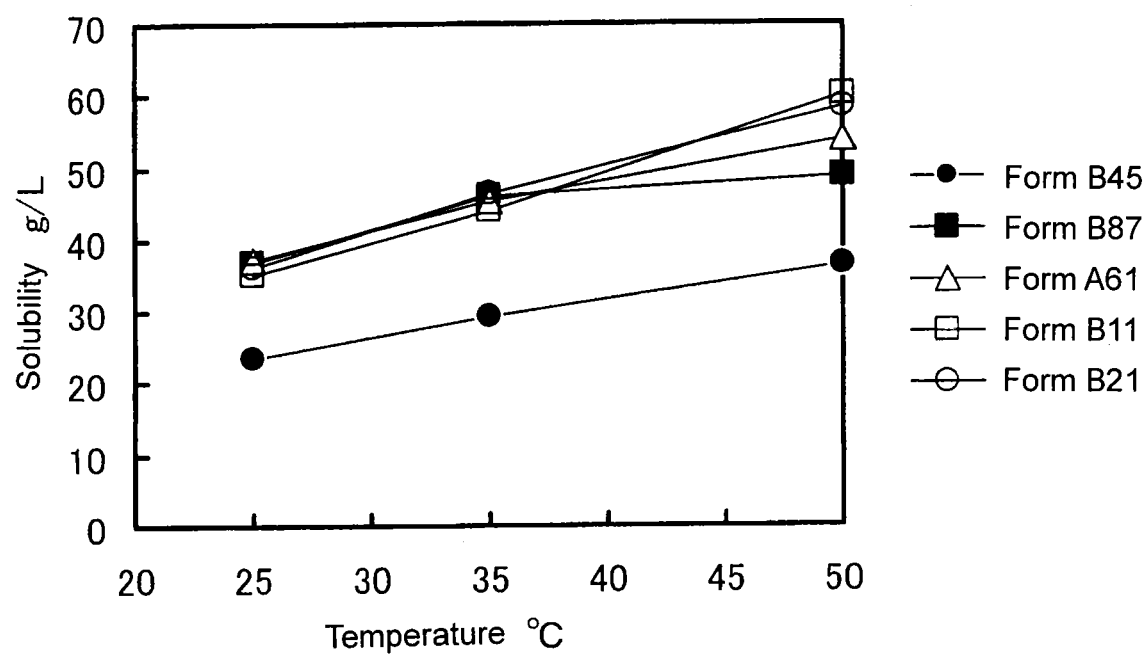
FIG. 1 shows a solubility of each crystal of hydrobromide of the present invention, added to a 84% aqueous EtOH solution at each temperature.
Figure 2:
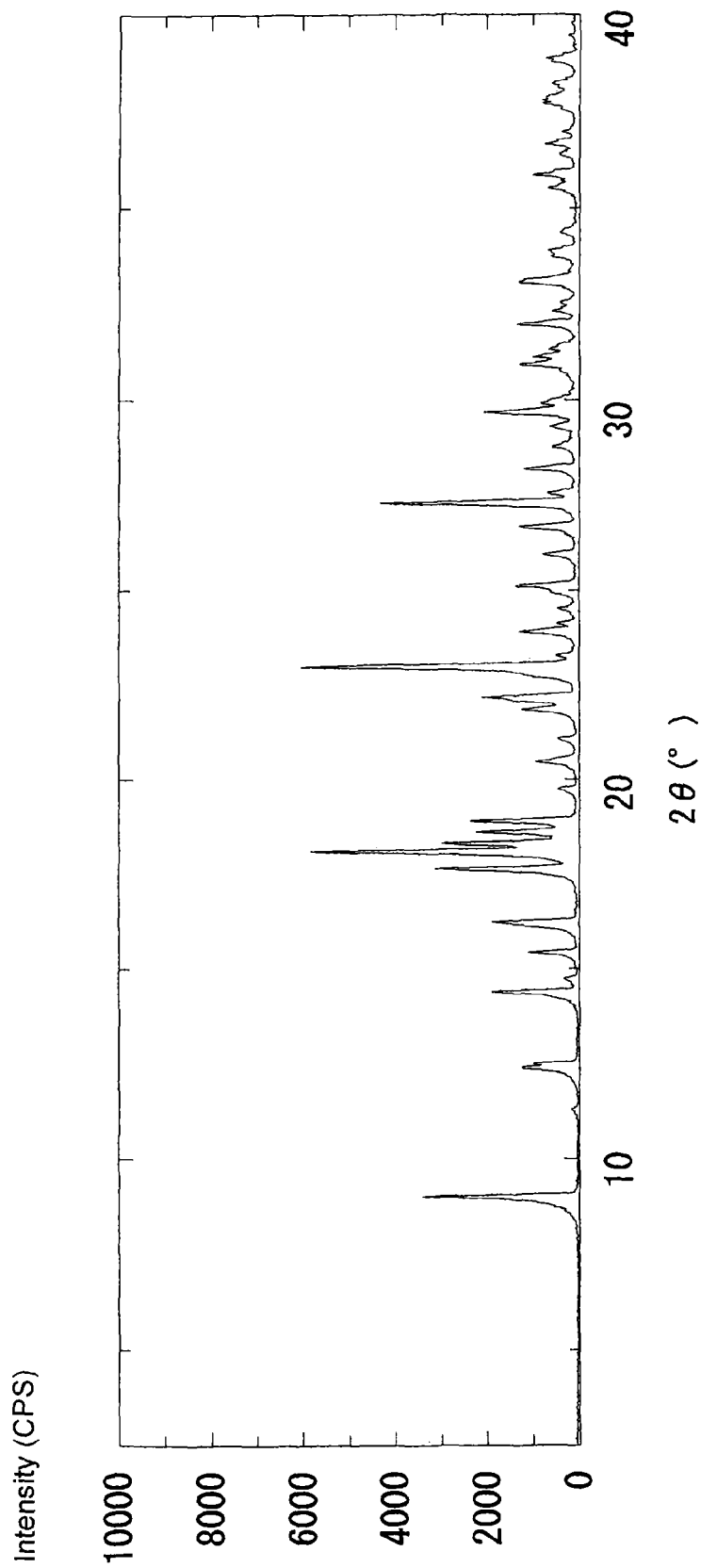
FIG. 2 shows a powder X-ray diffractogram of a Form B45 crystal of 4-{[(1R,2s,3S,5s,7s)-5-hydroxy-2-adamantyl]amino}-1H-pyrrolo[2,3-b]pyridine-5-carboxamide hydrobromide.
Figure 3:
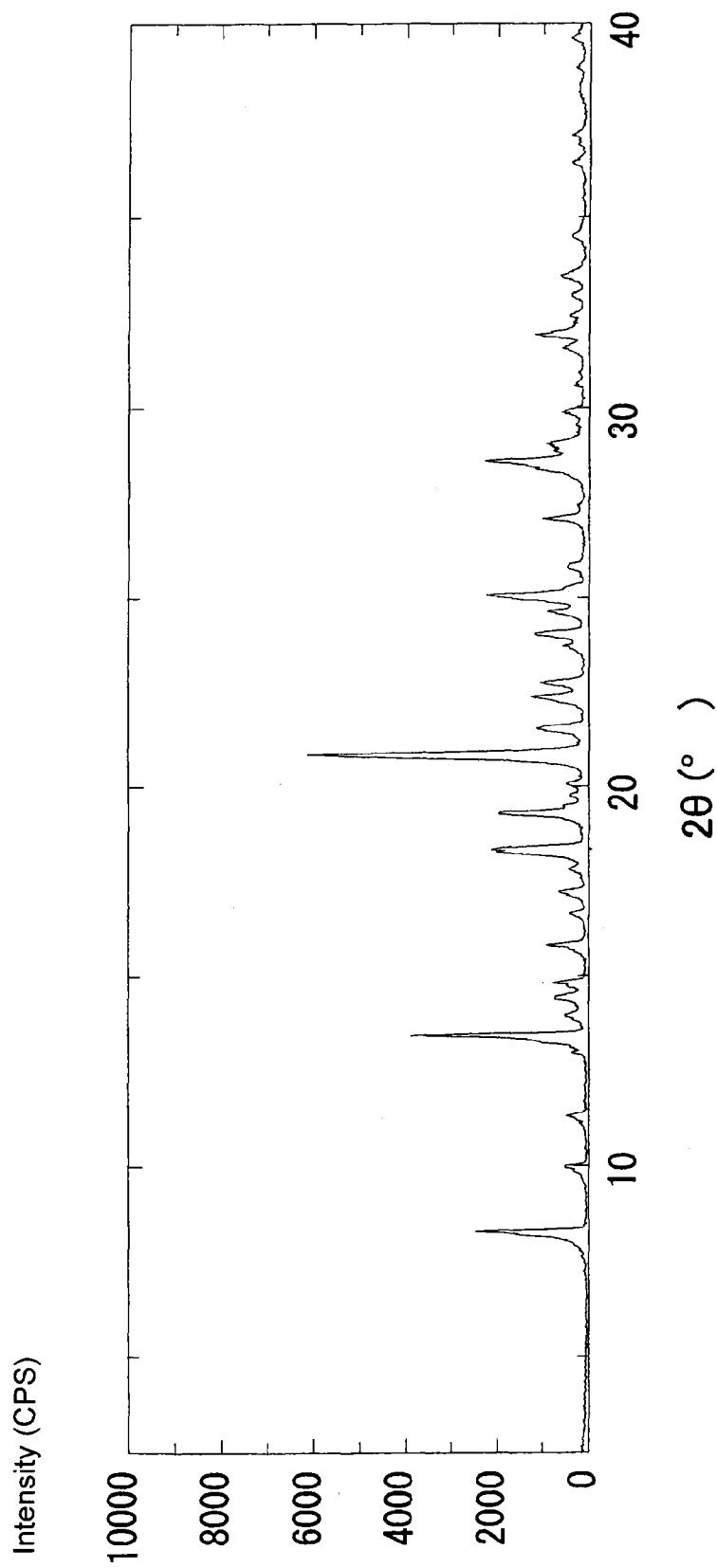
FIG. 3 shows a powder X-ray diffractogram of an Form A87 crystal of 4-{[(1R,2s,3S,5s,7s)-5-hydroxy-2-adamantyl]amino}-1H-pyrrolo[2,3-b]pyridine-5-carboxamide hydrobromide.
Figure 4:
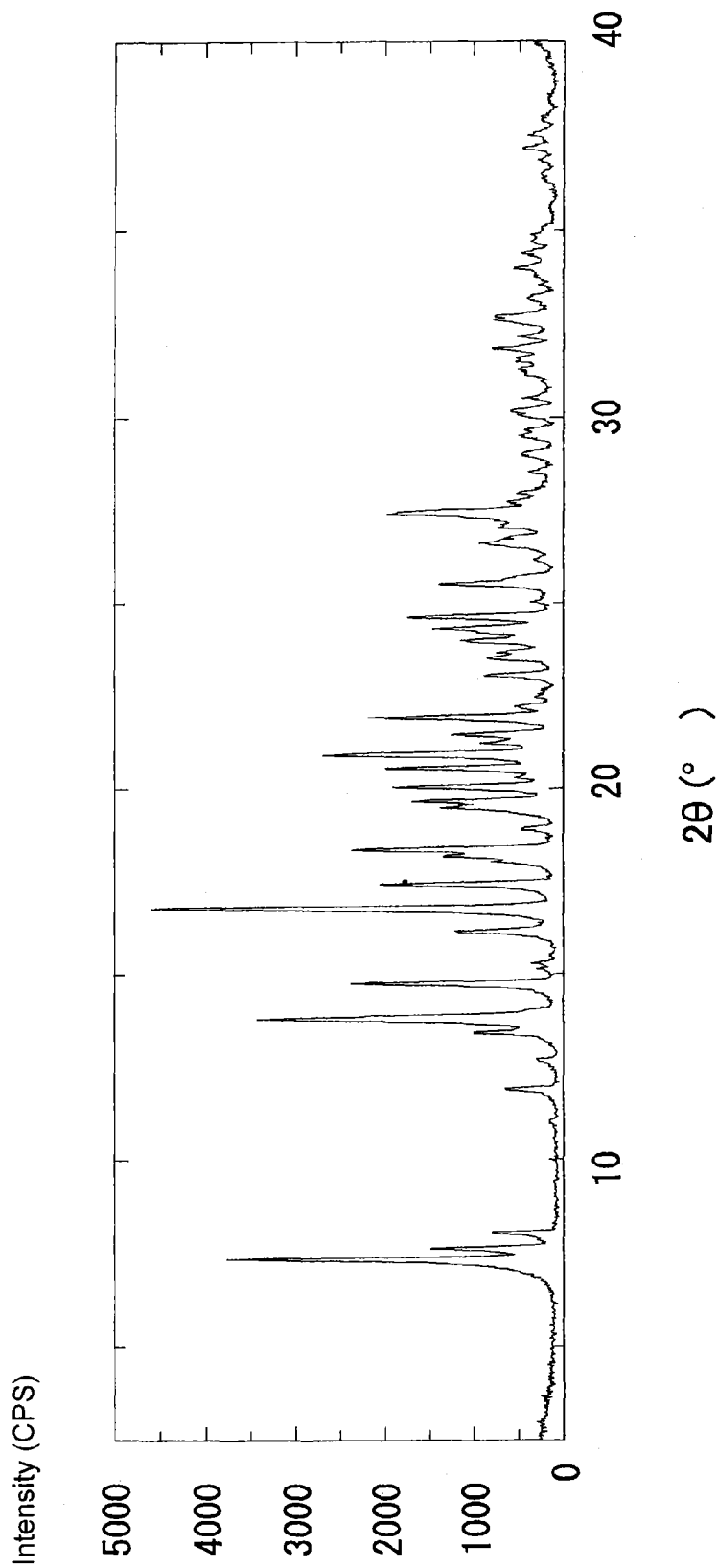
FIG. 4 shows a powder X-ray diffractogram of an Form A61 crystal of 4-{[(1R,2s,3S,5s,7s)-5-hydroxy-2-adamantyl]amino}-1H-pyrrolo[2,3-b]pyridine-5-carboxamide hydrobromide.
Figure 5:
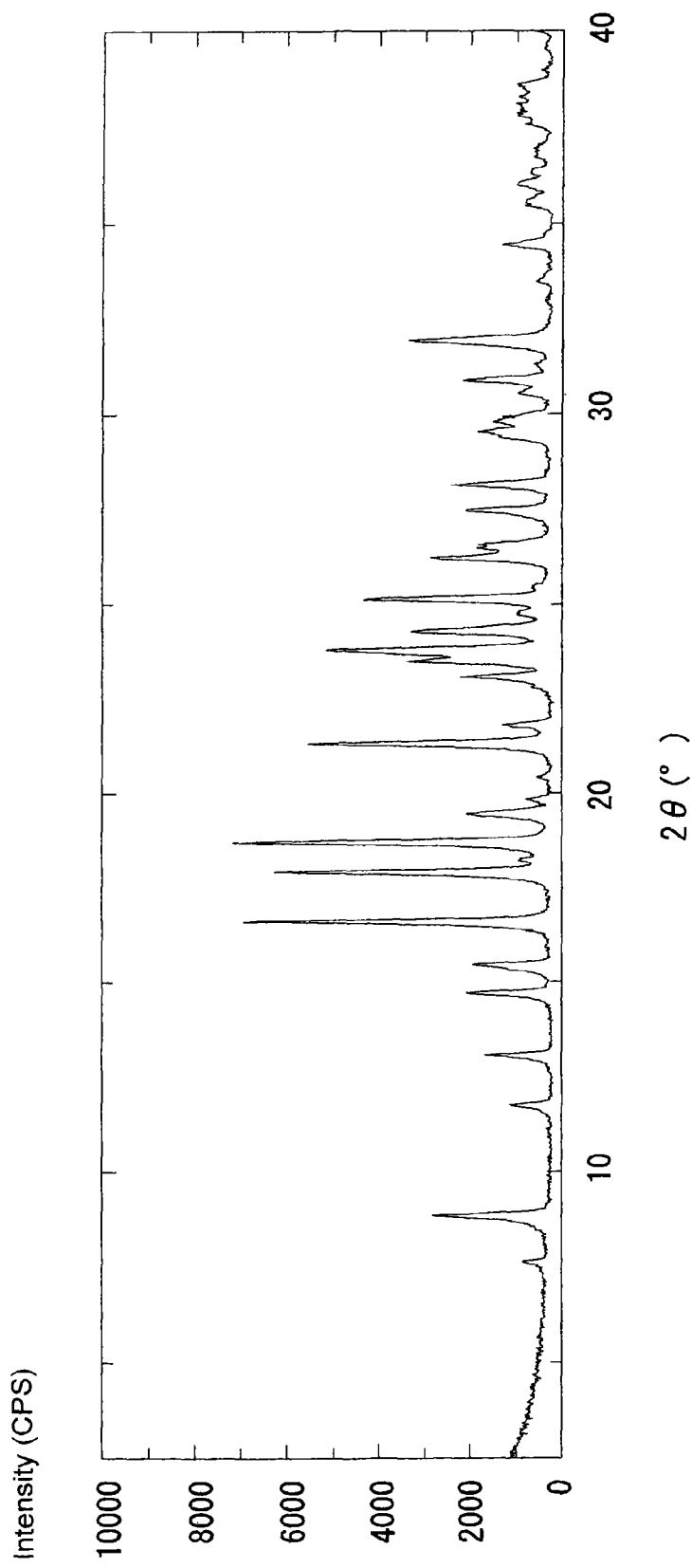
FIG. 5 shows a powder X-ray diffractogram of an Form A36 crystal of 4-{[(1R,2s,3S,5s,7s)-5-hydroxy-2-adamantyl]amino}-1H-pyrrolo[2,3-b]pyridine-5-carboxamide hydrobromide.
Figure 6:
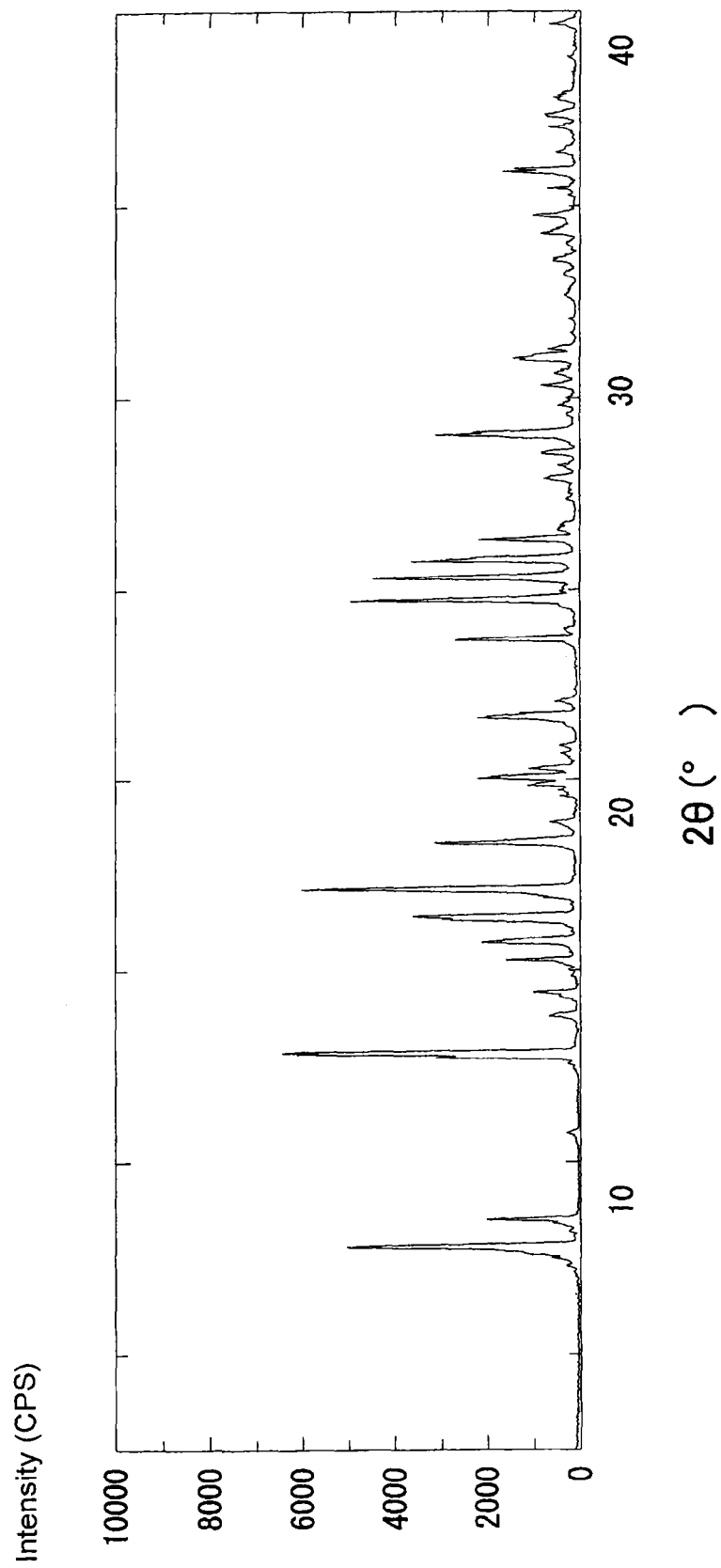
FIG. 6 shows a powder X-ray diffractogram of a Form B11 crystal of 4-{[(1R,2s,3S,5s,7s)-5-hydroxy-2-adamantyl]amino}-1H-pyrrolo[2,3-b]pyridine-5-carboxamide hydrobromide monohydrate.
Figure 7:
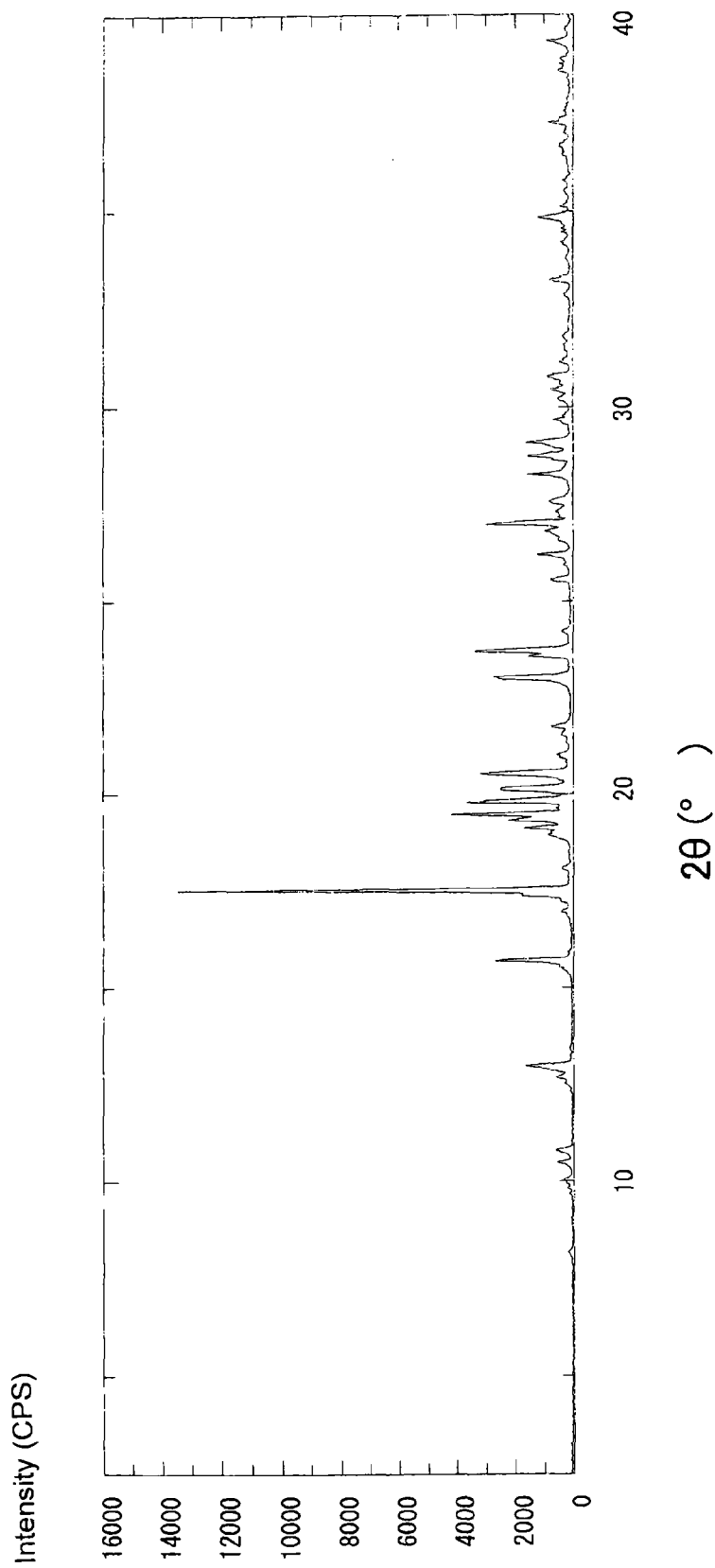
FIG. 7 shows a powder X-ray diffractogram of a Form B21 crystal of 4-{[(1R,2s,3S,5s,7s)-5-hydroxy-2-adamantyl]amino}-1H-pyrrolo[2,3-b]pyridine-5-carboxamide hydrobromide dihydrate.
Figure 8:
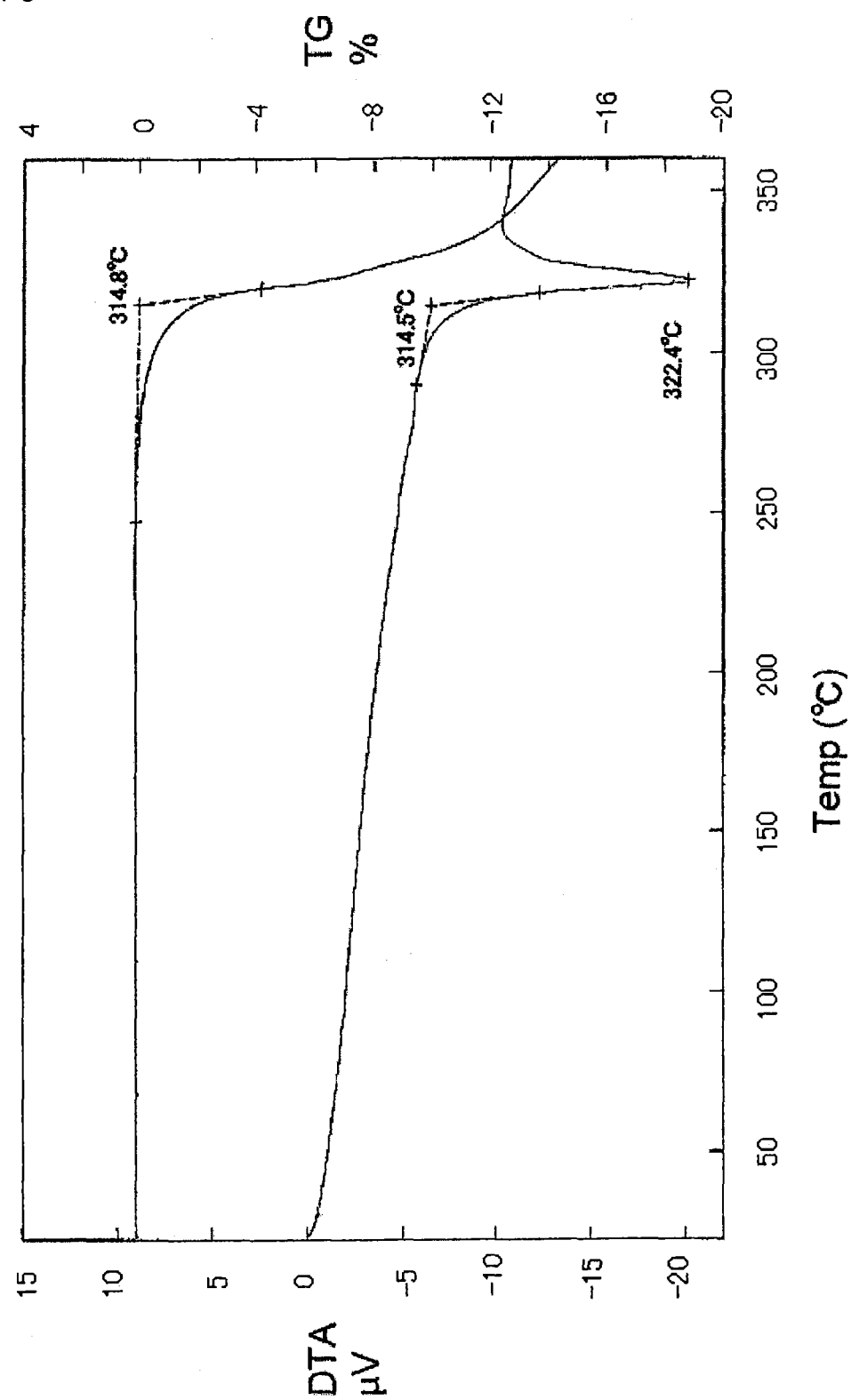
FIG. 8 shows a thermal analysis diagram of a Form B45 crystal of 4-{[(1R,2s,3S,5s,7s)-5-hydroxy-2-adamantyl]amino}-1H-pyrrolo[2,3-b]pyridine-5-carboxamide hydrobromide.
Figure 9:
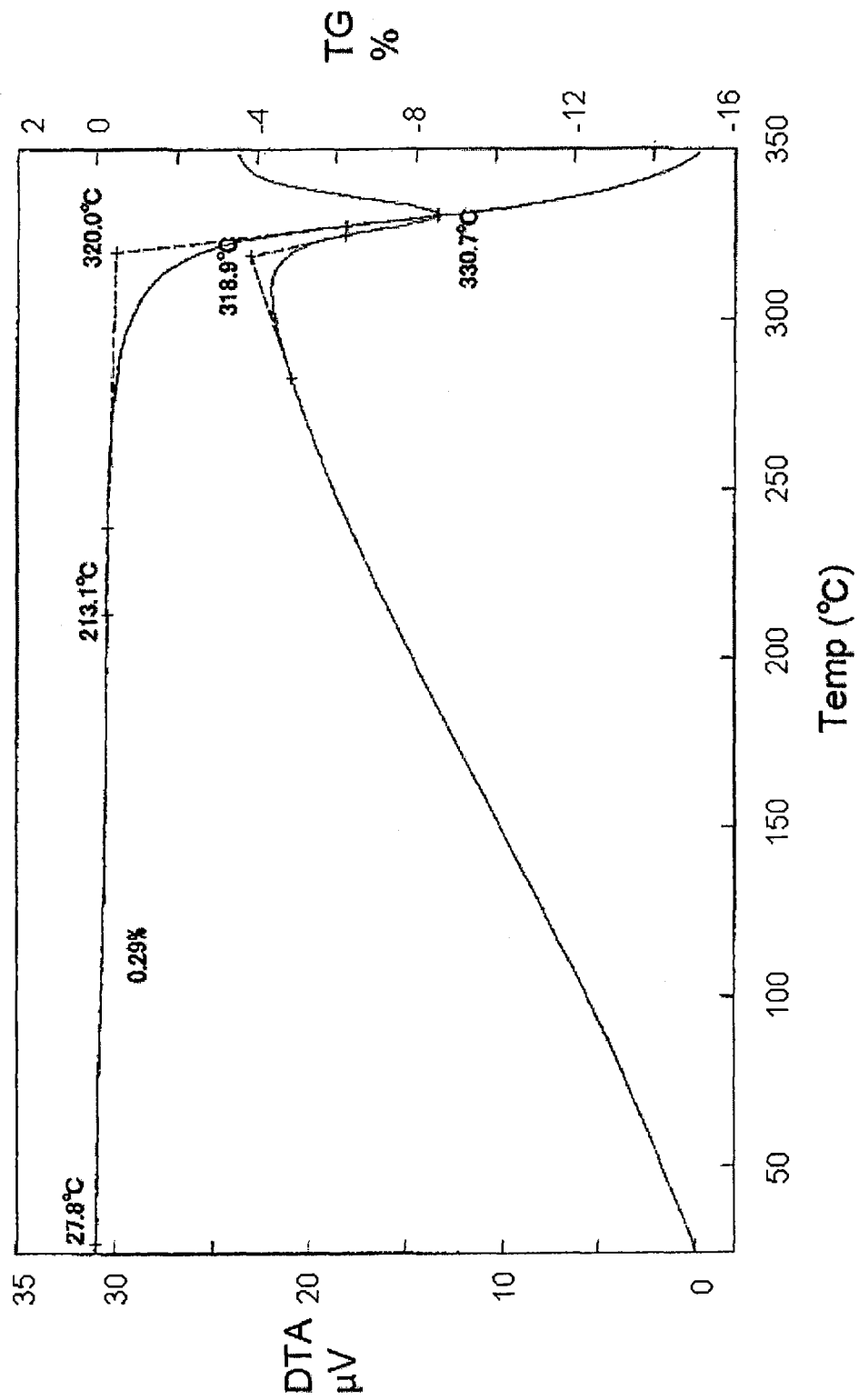
FIG. 9 shows a thermal analysis diagram of an Form A87 crystal of 4-{[(1R,2s,3S,5s,7s)-5-hydroxy-2-adamantyl]amino}-1H-pyrrolo[2,3-b]pyridine-5-carboxamide hydrobromide.
Figure 10:
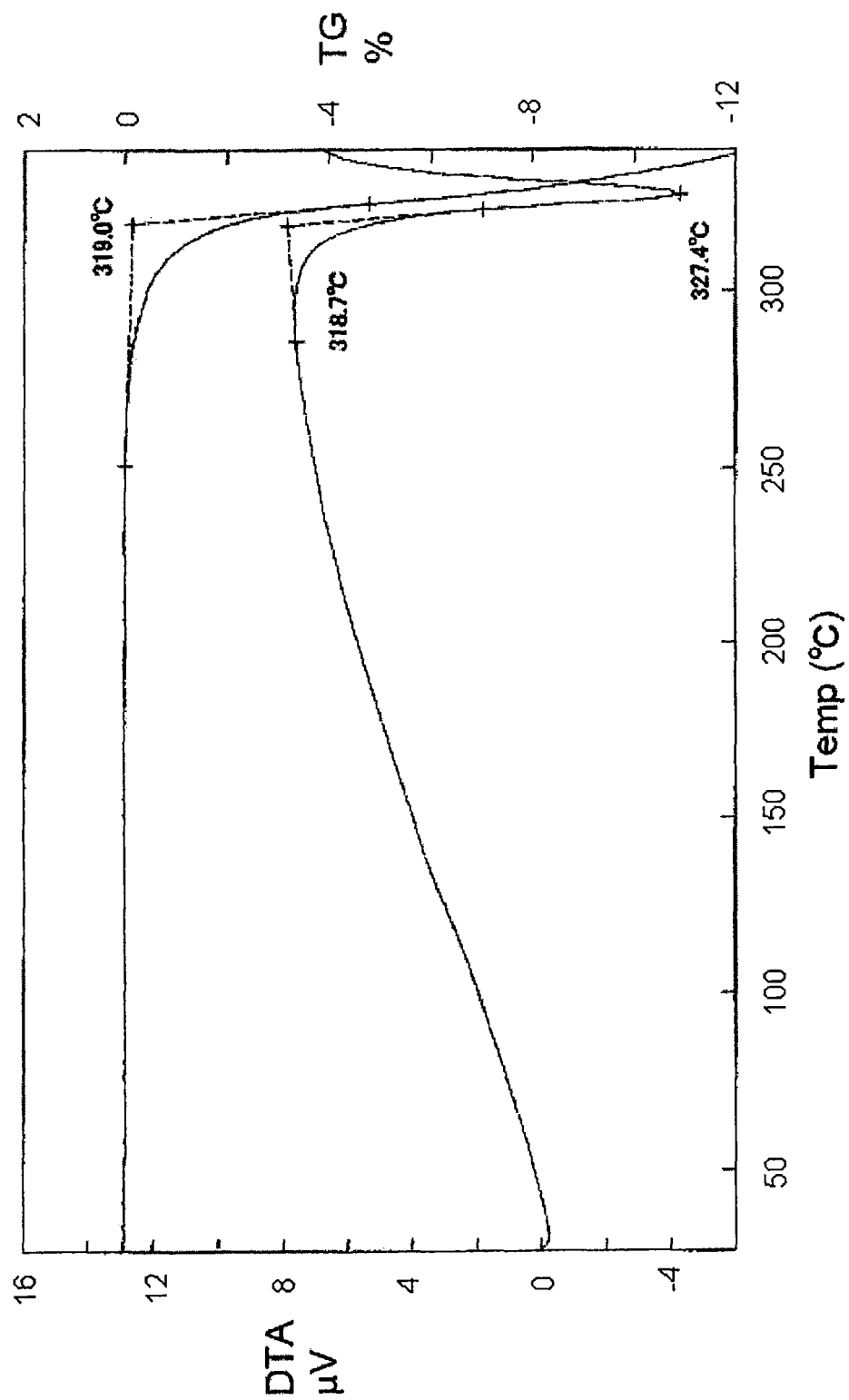
FIG. 10 shows a thermal analysis diagram of an Form A61 crystal of 4-{[(1R,2s,3S,5s,7s)-5-hydroxy-2-adamantyl]amino}-1H-pyrrolo[2,3-b]pyridine-5-carboxamide hydrobromide.
Figure 11:
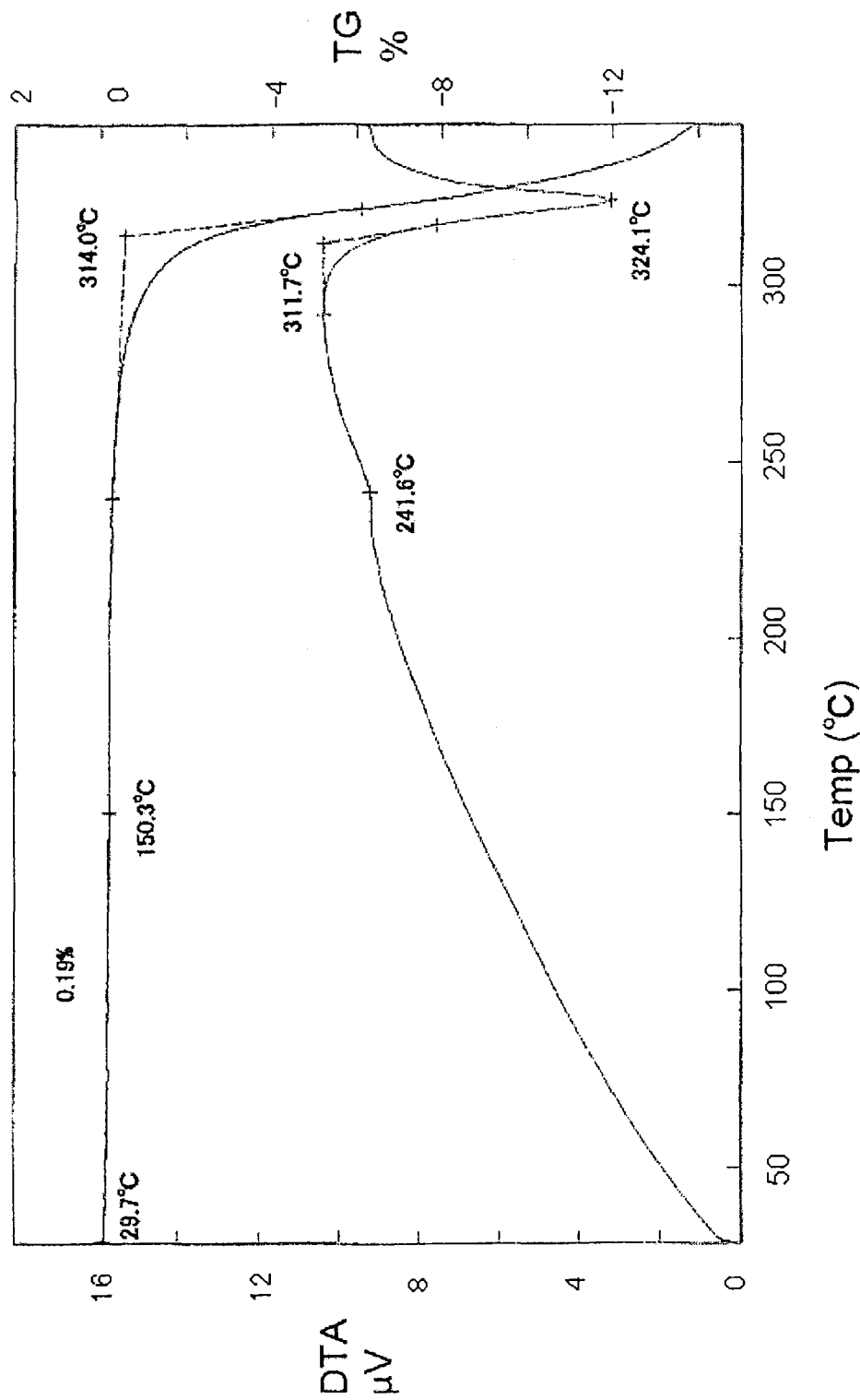
FIG. 11 shows a thermal analysis diagram of an Form A36 crystal of 4-{[(1R,2s,3S,5s,7s)-5-hydroxy-2-adamantyl]amino}-1H-pyrrolo[2,3-b]pyridine-5-carboxamide hydrobromide.
Figure 12:
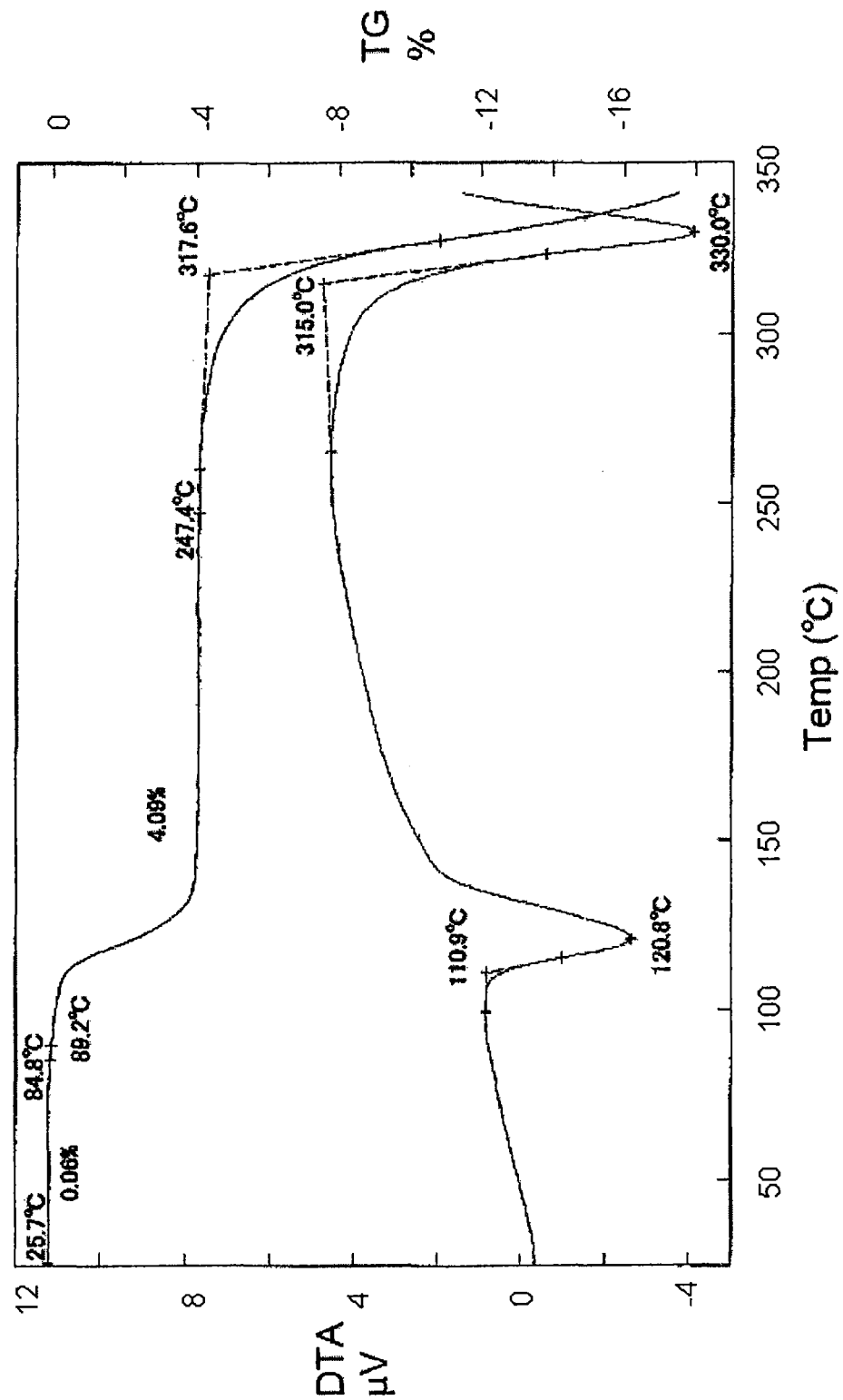
FIG. 12 shows a thermal analysis diagram of a Form B11 crystal of 4-{[(1R,2s,3S,5s,7s)-5-hydroxy-2-adamantyl]amino}-1H-pyrrolo[2,3-b]pyridine-5-carboxamide hydrobromide monohydrate.
Figure 13:
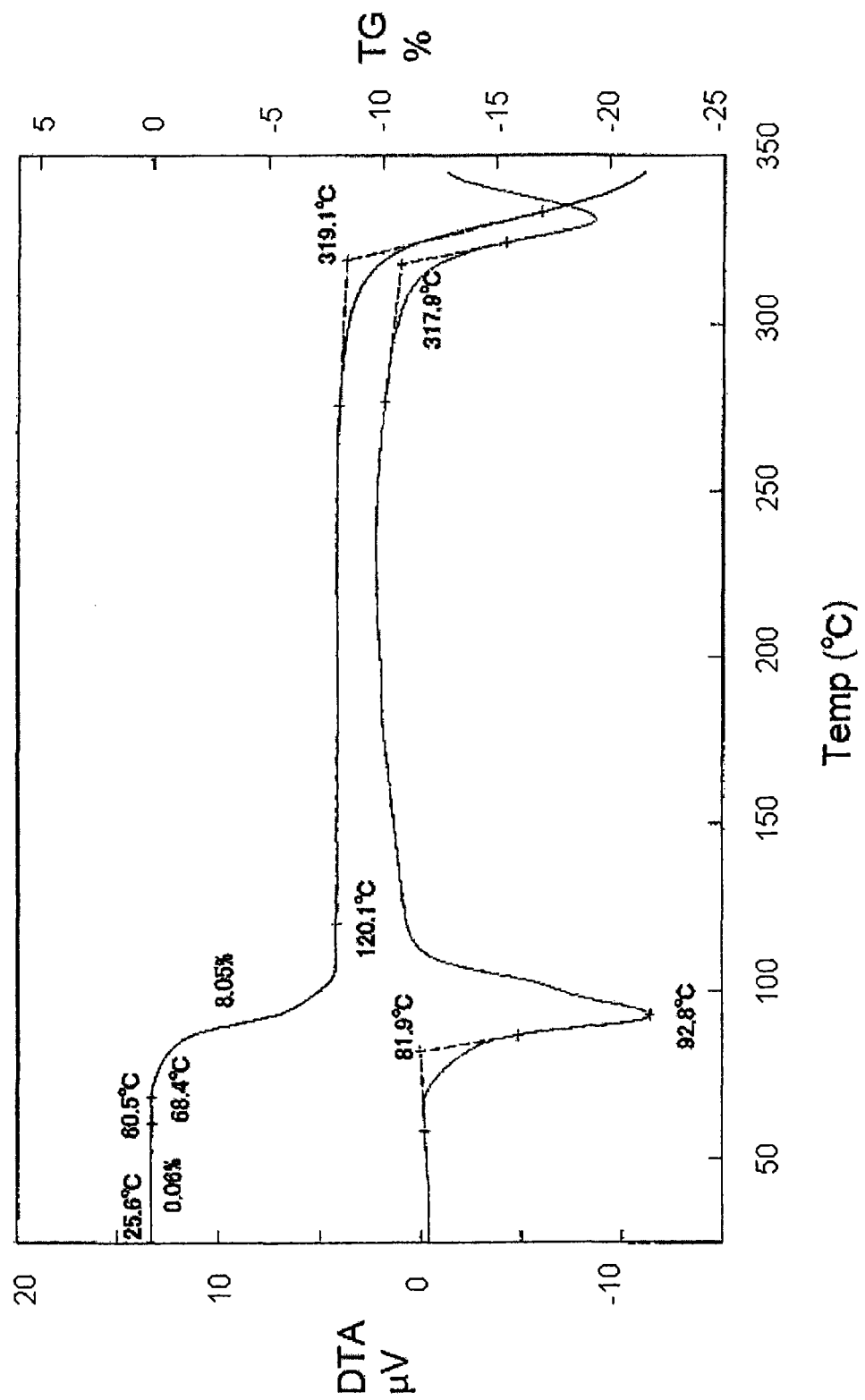
FIG. 13 shows a thermal analysis diagram of a Form B21 crystal of 4-{[(1R,2s,3S,5s,7s)-5-hydroxy-2-adamantyl]amino}-1H-pyrrolo[2,3-b]pyridine-5-carboxamide hydrobromide dihydrate.
Figure 14:
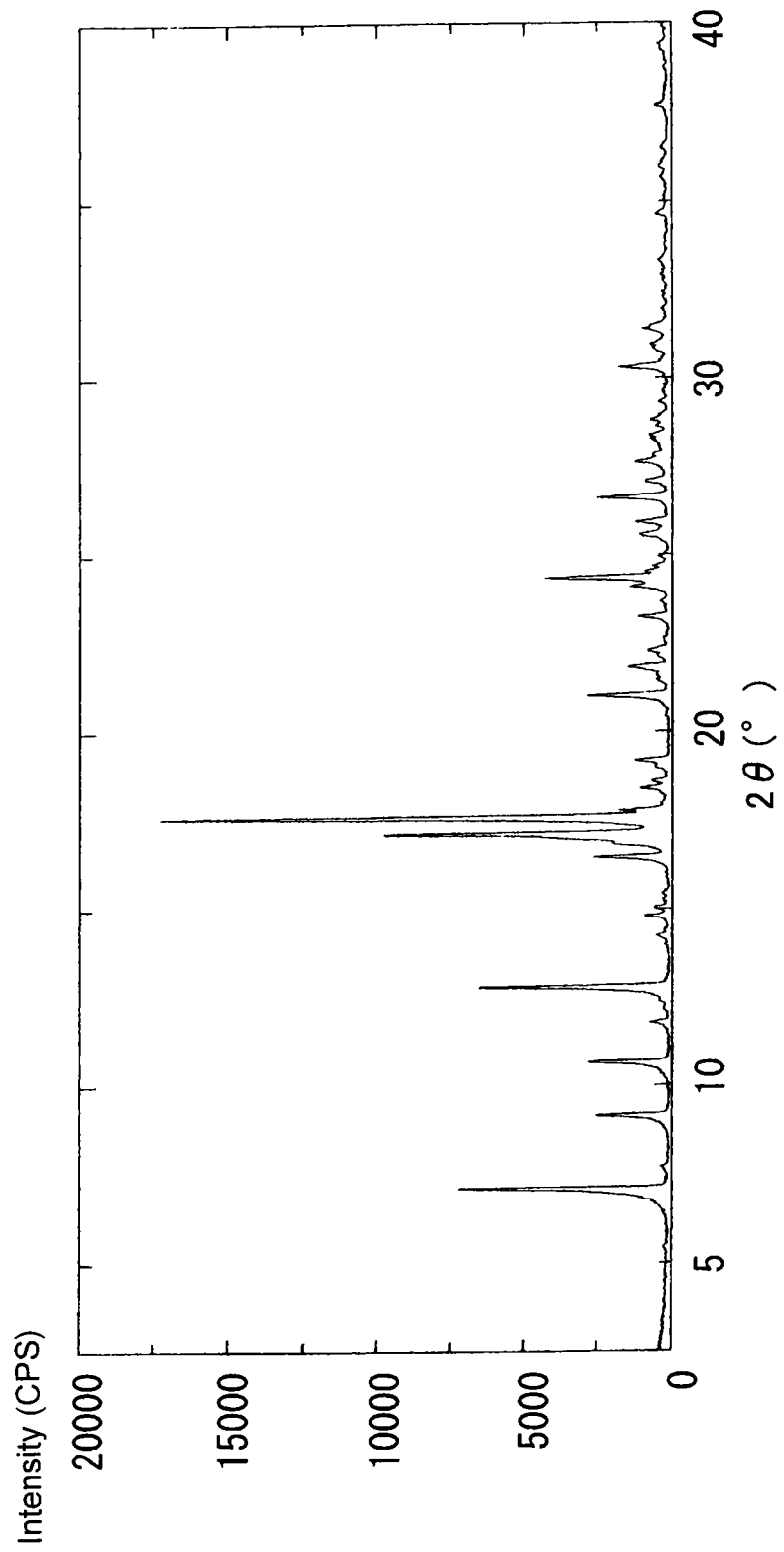
FIG. 14 shows a powder X-ray diffractogram of an Form A24 crystal of 4-{[(1R,2s,3S,5s,7s)-5-hydroxy-2-adamantyl]amino}-1H-pyrrolo[2,3-b]pyridine-5-carboxamide succinate.
Figure 15:
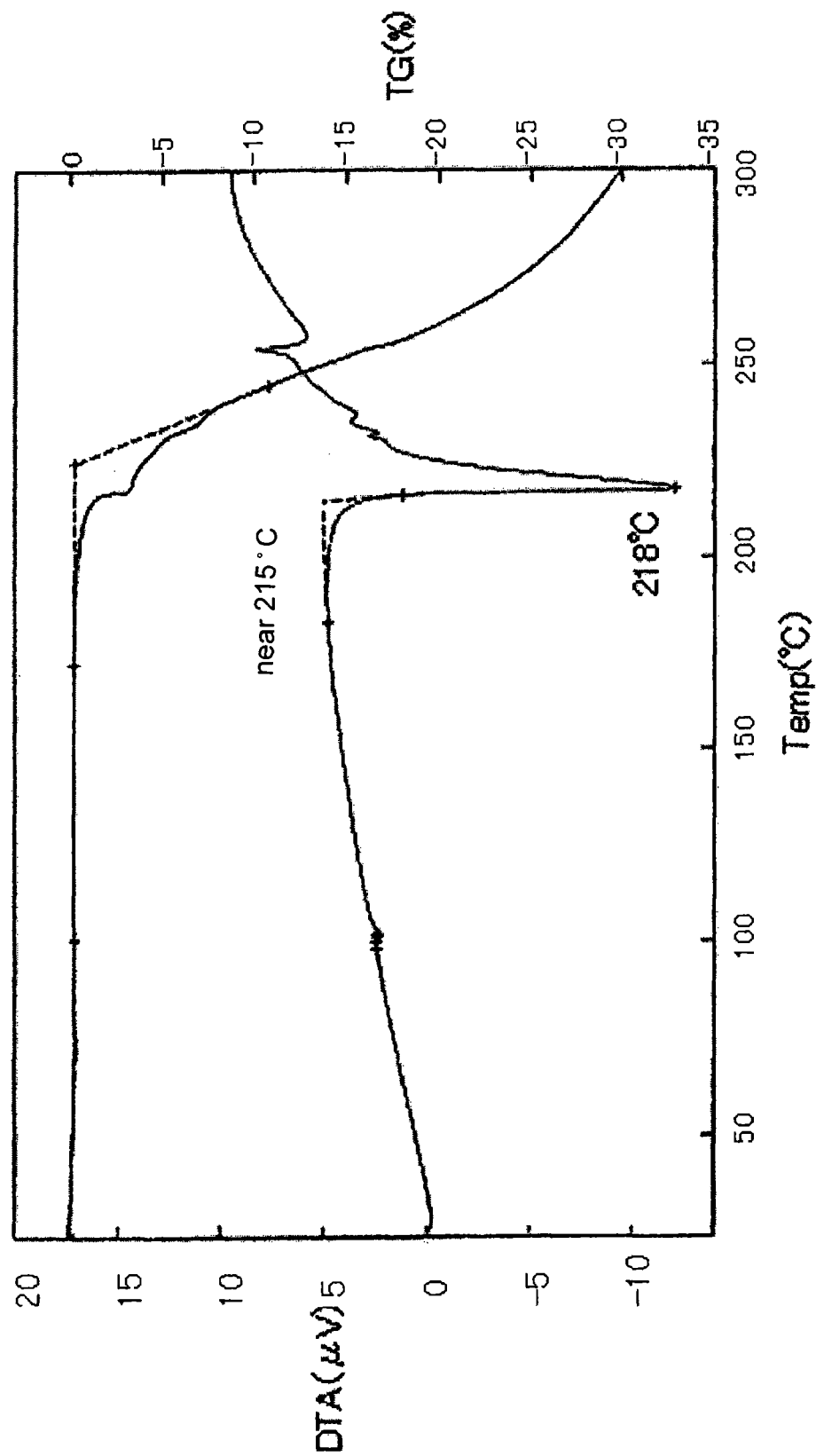
FIG. 15 shows a thermal analysis diagram of an Form A24 crystal of 4-{[(1R,2s,3S,5s,7s)-5-hydroxy-2-adamantyl]amino}-1H-pyrrolo[2,3-b]pyridine-5-carboxamide succinate.
Figure 16:
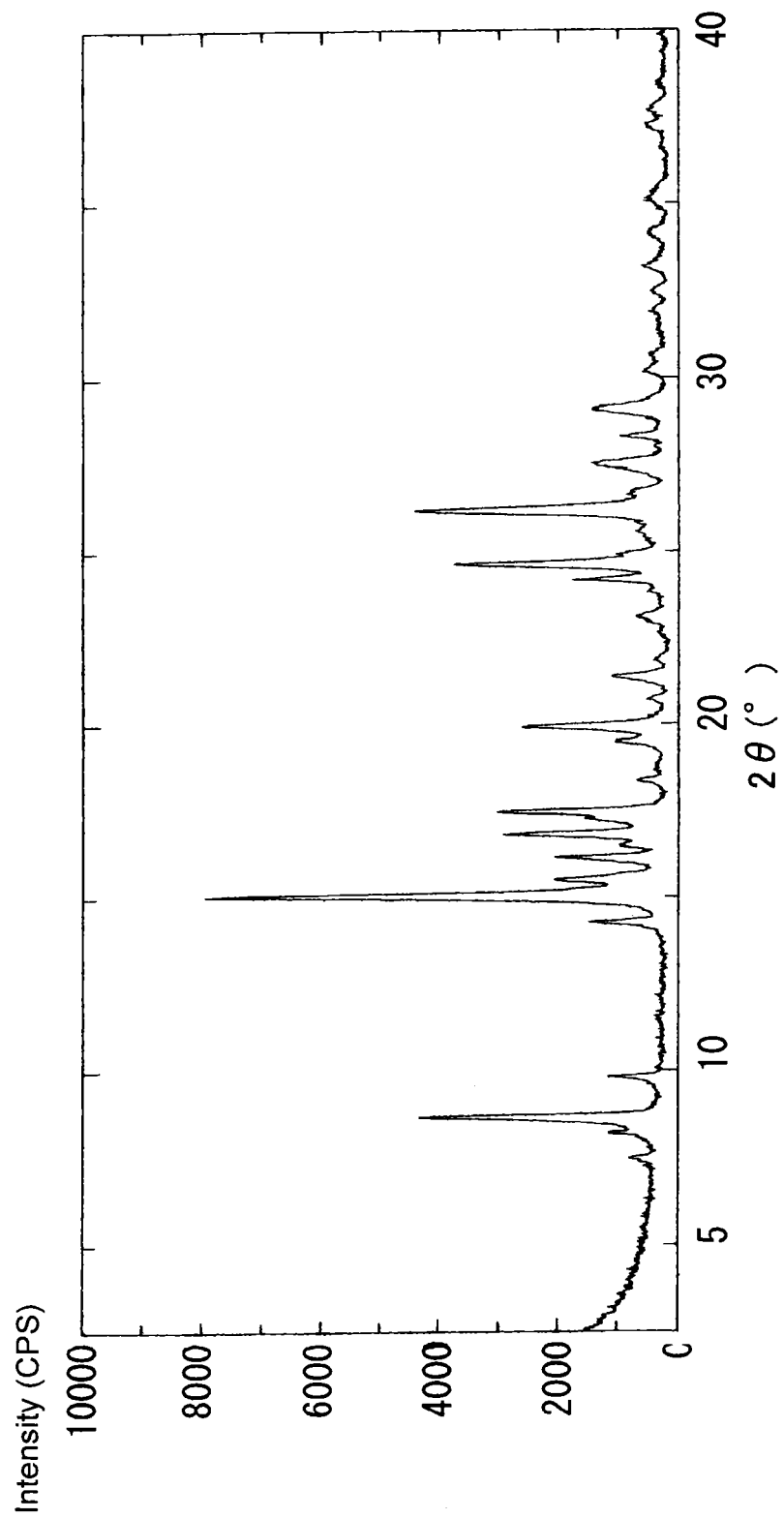
FIG. 16 shows a powder X-ray diffractogram of an Form A33 crystal of 4-{[(1R,2s,3S,5s,7s)-5-hydroxy-2-adamantyl]amino}-1H-pyrrolo[2,3-b]pyridine-5-carboxamide hydrochloride anhydride.
Figure 17:
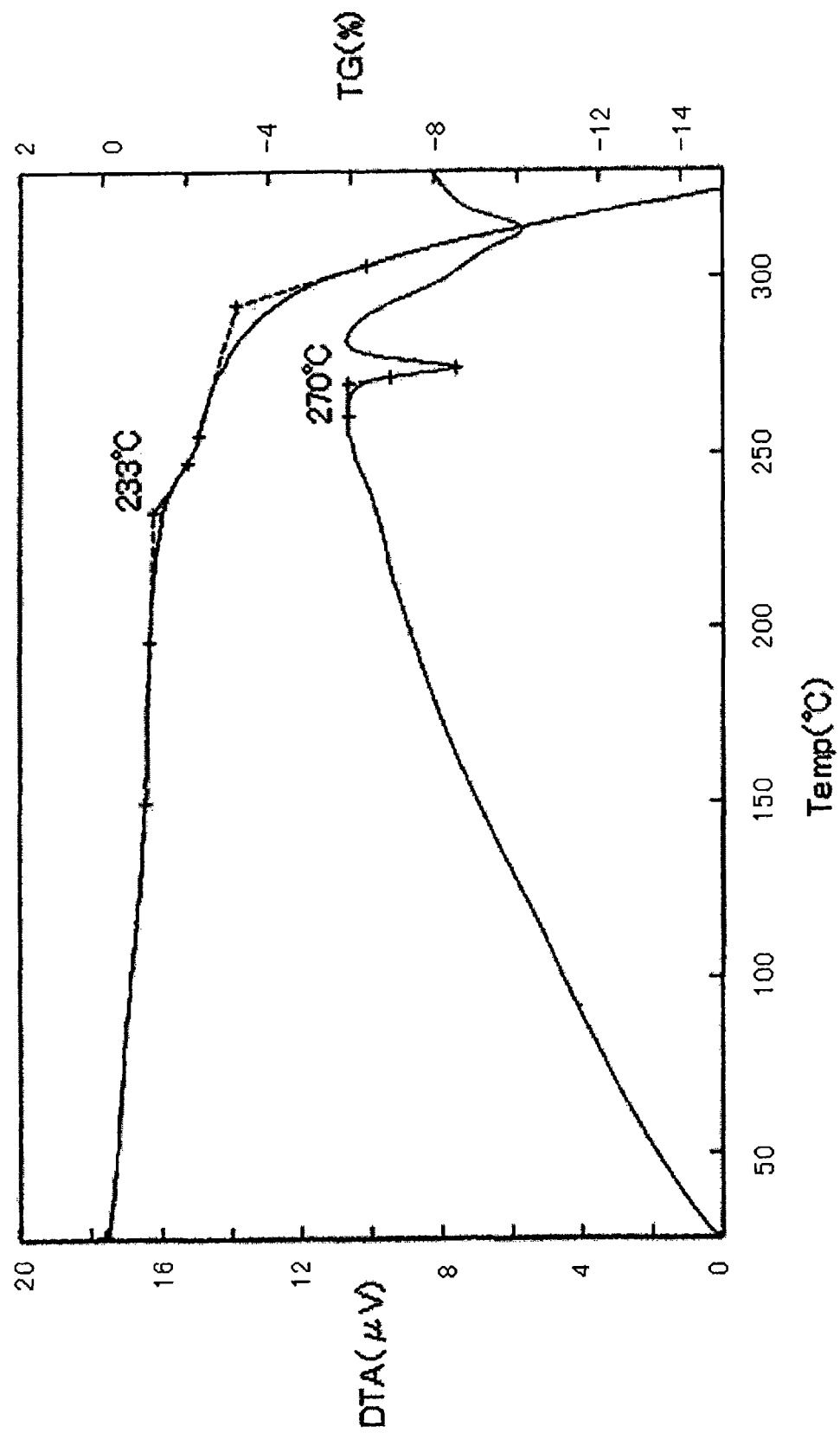
FIG. 17 shows a thermal analysis diagram of an Form A33 crystal of 4-{[(1R,2s,3S,5s,7s)-5-hydroxy-2-adamantyl]amino}-1H-pyrrolo[2,3-b]pyridine-5-carboxamide hydrochloride anhydride.
Figure 18:
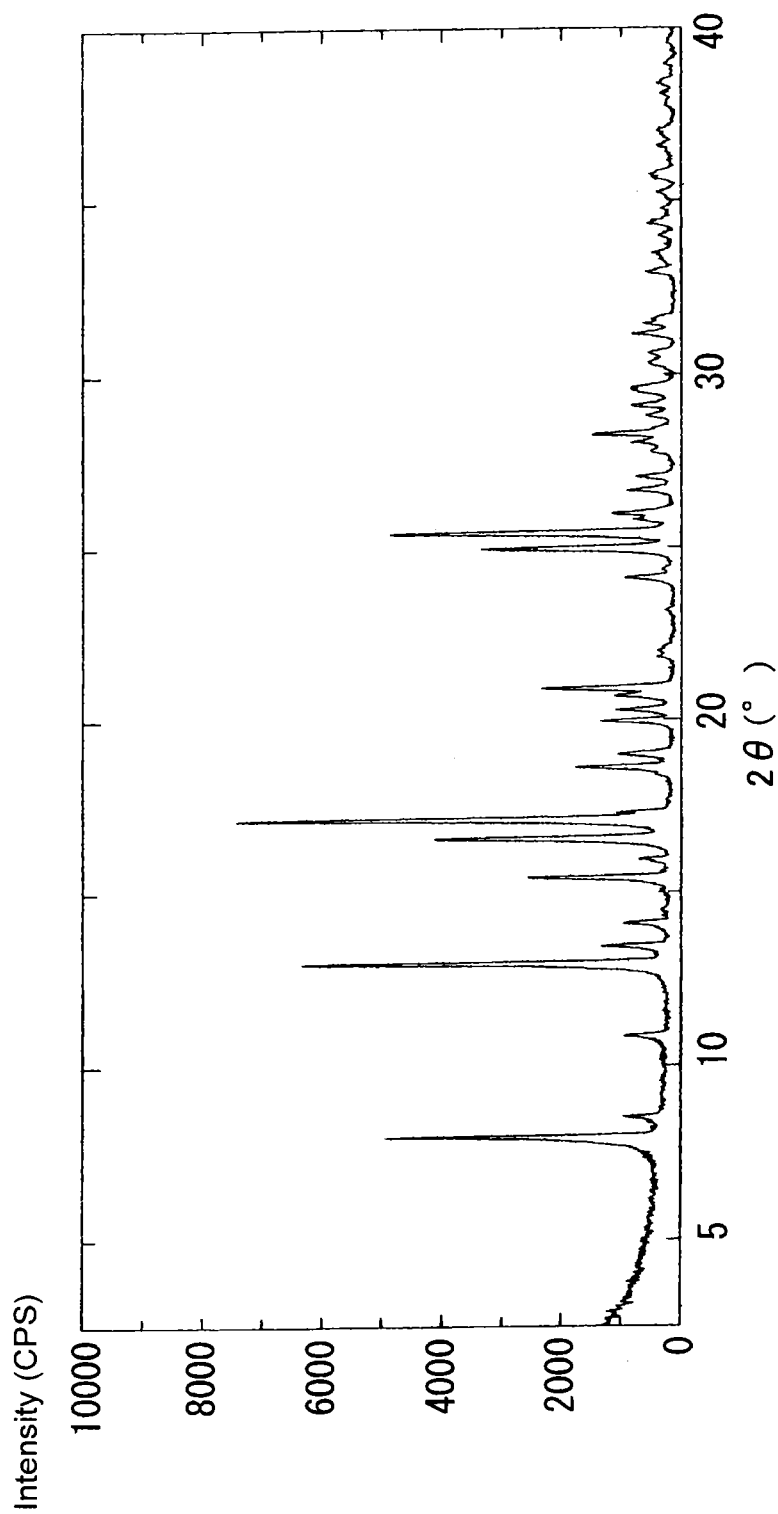
FIG. 18 shows a powder X-ray diffractogram of an Form A34 crystal of 4-{[(1R,2s,3S,5s,7s)-5-hydroxy-2-adamantyl]amino}-1H-pyrrolo[2,3-b]pyridine-5-carboxamide hydrochloride hydrate.
Figure 19:
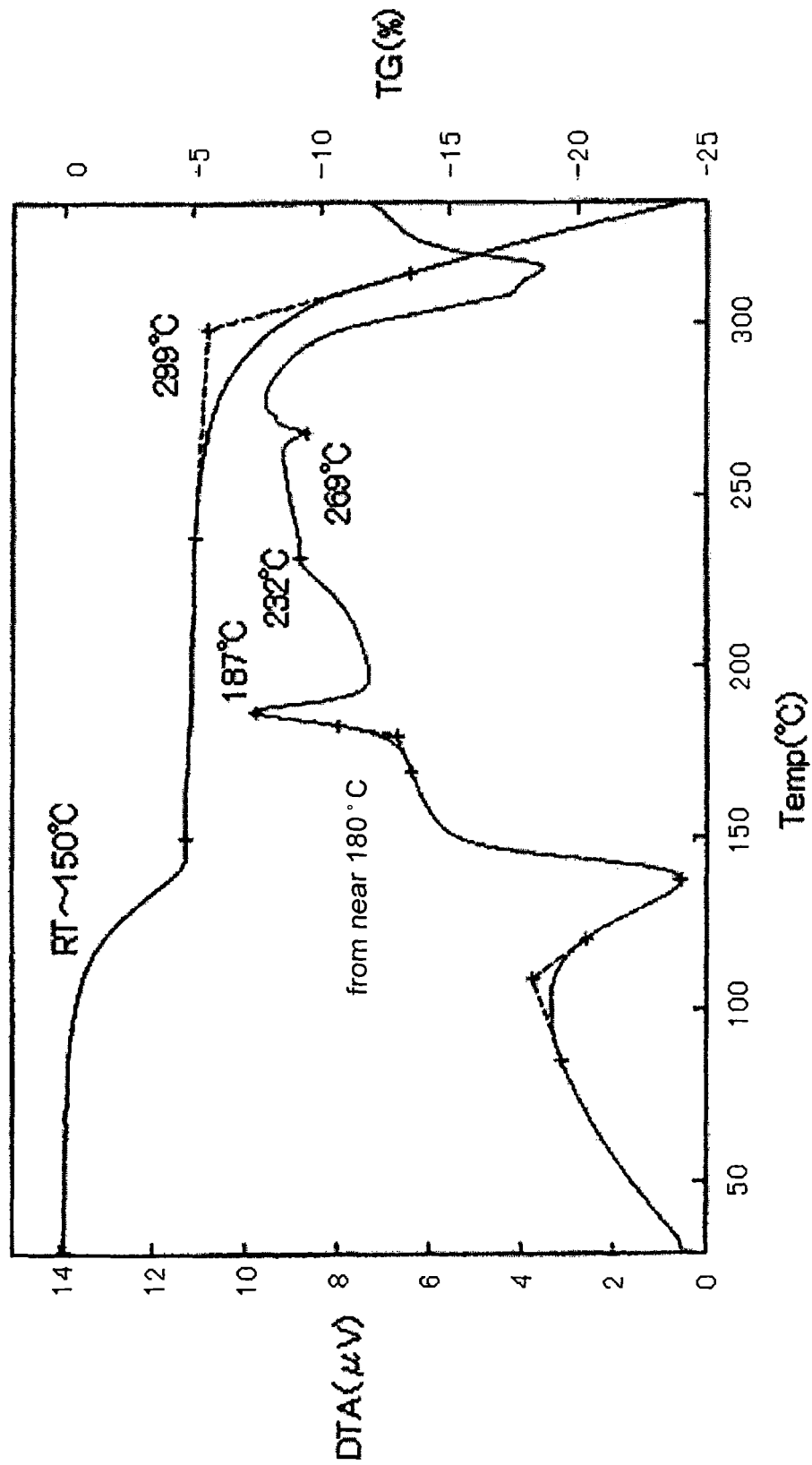
FIG. 19 shows a thermal analysis diagram of an Form A34 crystal of 4-{[(1R,2s,3S,5s,7s)-5-hydroxy-2-adamantyl]amino}-1H-pyrrolo[2,3-b]pyridine-5-carboxamide hydrochloride hydrate.

Hereinafter, the present invention will be described in detail.

In the present specification, the term "free form" refers to 4-{[(1R,2s,3S,5s,7s)-5-hydroxy-2-adamantyl]amino}-1H-pyrrolo[2,3-b]pyridine-5-carboxamide, which does not form a salt.

The term "hydrobromide" refers to 4-{[(1R,2s,3S,5s,7s)-5-hydroxy-2-adamantyl]amino}-1H-pyrrolo[2,3-b]pyridine-5-carboxamide hydrobromide.

The powder X-ray diffraction is measured using RIGAKU RINT-TTRII under the conditions of a tube: Cu, a tube current: 300 mA, a tube voltage, 50 kV, a sampling width: 0.02°, a scanning speed: 4°/min, a wavelength: 1.54056 angstroms, and a measurement diffraction angle (2θ): 2.5 to 40°.

NMR measurement was performed using a Varian INOVA600. In the NMR measurement, a chemical shift value was determined using TMS (tetramethylsilane) as an internal standard. MS measurement was performed using a Water Acquity UPLC-ZQ. Elemental analysis was performed using an Elementer Vario ELIII DIONEX DX-500.

Thermal analysis (TG/DTA) was performed under the following conditions.

EXSTAR TG/DTA6200, manufactured by SII Nanotechnology, Inc., from room temperature to 350°, a temperature rising speed: 10° C./min, $N_2$ (100 mL/min), and an aluminum sample pan.

For the hydrate, the water content was measured according to a Karl Fischer method described in the Japanese Pharmacopoeia.

(General Production Process)

Various salts of 4-{[(1R,2s,3S,5s,7s)-5-hydroxy-2-adamantyl]amino}-1H-pyrrolo[2,3-b]pyridine-5-carboxamide in the present invention can be prepared by the following method. 4-{[(1R,2s,3S,5s,7s)-5-hydroxy-2-adamantyl]amino}-1H-pyrrolo[2,3-b]pyridine-5-carboxamide is dissolved in a solvent which does not interfere with a reaction, and various acids are added thereto (in the case of a solid, they are dissolved in a polar solvent), followed by stirring at a constant temperature. The solution is heated and stirred in a warm bath at 70 to 100° C., and preferably 80° C. for 0.5 to 4 hours, and preferably 1 hour, usually under the condition of refluxing, then left to be cooled, and stirred. The solid obtained by using MeOH or MeCN as a polar solvent can be collected by filtration, and dried to obtain various salts of 4-{[(1R,2s,3S,5s,7s)-5-hydroxy-2-adamantyl]amino}-1H-pyrrolo[2,3-b]pyridine-5-carboxamide.

For example, 4-{[(1R,2s,3S,5s,7s)-5-hydroxy-2-adamantyl]amino}-1H-pyrrolo[2,3-b]pyridine-5-carboxamide hydrobromide in the present invention can be prepared by the following method.

[Chem. 2]

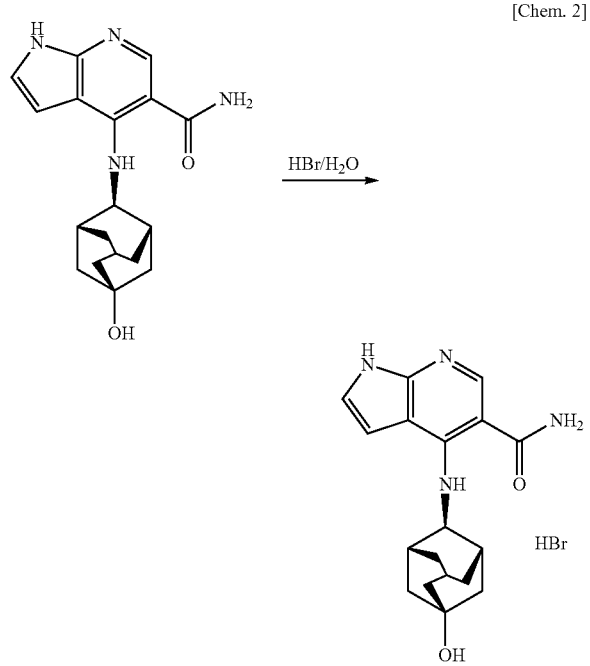

In a solvent which usually does not interfere with the reaction of an aqueous alcohol solution or the like, hydrobromic acid in a stoichiometrically equivalent amount or an excess amount is used, and 48% hydrobromic acid may be carefully added while keeping the reaction solution acidic in range of 0° C. with warming as a reaction temperature. For the acidity of the reaction solution, the pH is preferably in the range of 1.5 to 2.0.

The compound represented by the formula (I) is the geometric isomer as shown by the formula, but in some cases, there exist a mixture of the geometric isomer with different isomers. The salts and crystals of the present invention include salts and crystals of a mixture of the geometric isomers of the formula (I) and other isomers. In a certain embodiment, the salts and crystals are formed with a mixture having a proportion of the geometric isomers of the formula (I) of 70% or more, 80% or more, 90% or more, 95% or more, 97% or more, 98% or more, or 99% or more. In another embodiment, the salts and crystals are the salts and crystals of the geometric isomer compounds of the formula (I), which are substantially pure.

As described in Patent Document 1, from the viewpoint that the compound represented by the formula (I) of the present invention has a JAK3 inhibitory action, the salt or crystal of the formula (I) of the present invention can be used for, for example, treatment of diseases caused by undesirable cytokine signaling, for example, rejection during live-donor transplantation, autoimmune diseases, asthma, atopic dermatitis, atherosclerosis, psoriasis, rheumatism, or diseases caused by abnormal cytokine signaling, such as cancer and leukemia, and the like.

A pharmaceutical composition containing one or two or more kinds of the salt or crystal of the formula (I) of the present invention can be prepared using excipients that are usually used in the art, that is, excipients for pharmaceutical preparations, carriers for pharmaceutical preparations, and the like according to the methods usually used.

Administration can be accomplished either by oral administration via tablets, pills, capsules, granules, powders, solutions, and the like, or parenteral administration, such as injections such as intraarticular, intravenous, and intramuscular injections, suppositories, ophthalmic solutions, eye ointments, transdermal liquid preparations, ointments, transdermal patches, transmucosal liquid preparations, transmucosal patches, inhalers, and the like.

The solid preparation for use in the oral administration according to the present invention is used in the form of tablets, powders, granules, capsules, or the like. In such a solid composition, one or more active ingredient(s) are mixed with at least one inactive excipient, such as lactose, mannitol, glucose, hydroxypropyl cellulose, microcrystalline cellulose, starch, polyvinylpyrrolidone, and/or magnesium aluminometasilicate. In a conventional method, the composition may contain inactive additives, such as a lubricant such as magnesium stearate, a disintegrating agent such as sodium carboxymethyl starch and the like, a stabilizer, or a solubilization assisting agent. If necessary, tablets or pills may be coated with sugar or a film of a gastric-soluble or enteric coating substance.

The liquid composition for oral administration contains pharmaceutically acceptable emulsions, solutions, suspensions, syrups, elixirs, or the like, and also contains generally used inert diluents, for example, purified water or EtOH. In addition to the inert diluent, the liquid composition may also contain auxiliary agents, such as a solubilization assisting agent, a moistening agent, and a suspending agent, sweeteners, flavors, aromatics, or antiseptics.

The injections for parenteral administration include sterile aqueous or non-aqueous solutions, suspensions and emulsions. The aqueous solvent includes, for example, distilled water for injection and physiological saline. Examples of the non-aqueous solvent include propylene glycol, polyethylene glycol, plant oils such as olive oil, alcohols such as EtOH, Polysorbate 80 (Japanese Pharmacopeia), and the like. Such a composition may further contain a tonicity agent, an antiseptic, a moistening agent, an emulsifying agent, a dispersing agent, a stabilizer, or a solubilization assisting agent. These are sterilized, for example, by filtration through a bacteria retaining filter, blending in of a bactericide, or irradiation. In addition, these can also be used by preparing a sterile solid composition, and dissolving or suspending it in sterile water or a sterile solvent for injection prior to its use.

The agent for external use includes ointments, plasters, creams, jellies, poultices, sprays, lotions, eye drops, and eye ointments. The agents contain generally used ointment bases, lotion bases, aqueous or non-aqueous liquid preparations, suspensions, and emulsions. Examples of the ointment bases or the lotion bases include polyethylene glycol, propylene glycol, white vaseline, bleached beeswax, polyoxyethylene hydrogenated castor oil, glyceryl monostearate, stearyl alcohol, cetyl alcohol, lauromacrogol, and sorbitan sesquioleate.

As the transmucosal agents such as an inhaler and a transnasal agent, those in the form of a solid, liquid, or semi-solid state are used, and can be prepared in accordance with a conventionally known method. For example, a known excipient, and also a pH adjusting agent, an antiseptic, a surfactant, a lubricant, a stabilizer, a thickening agent, or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a known device or sprayer, such as a measured administration inhalation device. A dry powder inhaler or the like may be for single or multiple administration use, and a dry powder or a powder-containing capsule may be used. Alternatively, this may be in a form such as a pressurized aerosol spray which uses an appropriate ejection agent, for example, a suitable gas such as chlorofluoroalkane, hydrofluoroalkane, and carbon dioxide.

A preferred embodiment of the present invention is a solid preparation for oral administration which includes the salt or crystal of the present invention.

A preferred embodiment of the present invention is a solid dispersion preparation using the salt or crystal of the present invention. The solid dispersion preparation refers to a preparation having a drug as a solid dispersion with a technique for sufficiently improving the solubility of a poorly soluble drug and ensuring the high dose. Specifically, it is a method, in which the salt or crystal of the present invention and a carrier (a water-soluble polymer carrier such as polyvinylpyrrolidone and hydroxypropylmethylcellulose) are dissolved in a co-solvent (for example, EtOH and an acetone-based solvent), and dried by a technique such as spray-drying to disperse and fix the compound of the formula (I) in the carrier, thereby temporarily improving the solubility to a supersaturated state. In a certain embodiment, the solid dispersion preparation of the present invention is a capsule, a fine particle, a granule, or a tablet, each using the solid dispersion prepared using the salt or crystal of the present invention. For example, the method described in JP-A-2004-083601 or JP-A-56-49314 can be employed.

Typically, in the case of oral administration, the daily dose of the salt or crystal of the compound (I) of the present invention is appropriately from about 0.001 to 100 mg/kg, preferably from 0.1 to 30 mg/kg, and more preferably 0.1 to 10 mg/kg, per body weight, administered in one portion or in 2 to 4 separate portions. In the case of intravenous administration, the daily dose is suitably administered from about 0.0001 to 10 mg/kg per body weight, once a day or two or more times a day. In addition, a transmucosal agent is administered at a dose from about 0.001 to 100 mg/kg per body weight, once a day or two or more times a day. The dose is appropriately decided upon in response to the individual case by taking the symptoms, the age, and the gender, and the like into consideration.

Moreover, the salt or crystal of the compound (I) of the present invention can be used in combination with various agents for treating or preventing the diseases for which the compound (I) is considered to be effective, as described above. Examples of the agents that can be used in combination may include, but are not limited to, cyclosporin A, tacrolimus, sirolimus, everolimus, micophenolate, azathioprine, brequinar, leflunomide, fingolimod, an anti-IL-2 receptor antibody (for example, daclizumab), an anti-CD3 antibody (for example, OKT3), anti-T cell immunogloblin (for example, AtGam), aspirin, acetaminophen, ibuprofen, naproxen, piroxicam, and an anti-inflammatory steroid (for example, prednisolone or dexamethasone). The combined preparations may be administered simultaneously, administered separately and continuously, or administered at a desired time interval. The preparations to be administered simultaneously may be a blend, or may be prepared individually.

EXAMPLES

Hereinbelow, the preparation methods for the salt or crystal of the compound (I) of the present invention will be described in more detail with reference to Examples. Further, the present invention is not limited to the salts or crystals described in Examples below. Further, the production processes of the starting compounds are each shown in Preparation Examples.

In the present specification, the following abbreviations may be used in some cases in the Examples, Preparation Examples, and Tables below. EtOH=ethanol, EtOAc=ethyl acetate, Et$_2$O=diethyl ether, MeCN=acetonitrile, MEK=methyl ethyl ketone, MgSO$_4$=anhydrous magnesium sulfate, NMP=N-methylpyrrolidone, DTA=differential thermal analysis, TG=thermogravimetry, TGA=thermogravimetry analyzer, LC=liquid chromatography, and RH=relative humidity.

Example 1

Method for Preparing Form B45 Crystal of Hydrobromide (In Case of Adding Seed Crystal)

After purging with nitrogen, 4-{[(1R,2s,3S,5s,7s)-5-hydroxy-2-adamantyl]amino}-1H-pyrrolo[2,3-b]pyridine-5-carboxamide (145.0 kg), water (377 L), EtOH (1508 L), and 48% hydrobromic acid (74.9 kg) were sequentially put into a reaction vessel at a room temperature, followed by starting stirring. While carefully keeping the pH in the range of 1.5 to 1.9, 48% hydrobromic acid was added thereto. The reaction mixture was warmed until the internal temperature reached 70° C. or higher, followed by stirring. After confirming the completion of dissolution, the mixture was stirred for 5 minutes or more, the dissolution liquid was clarified and filtered at an internal temperature of 70° C. or higher, and the reaction vessel line was washed with warm EtOH (290 L). At an internal temperature of about 50° C., a seed crystal (Form B45, 145 g) of 4-{[(1R,2s,3S,5s,7s)-5-hydroxy-2-adamantyl]amino}-1H-pyrrolo[2,3-b]pyridine-5-carboxamide hydrobromide was added thereto, followed by aging and stirring at an internal temperature of 40 to 50° C. overnight. The mixture was subsequently cooled to an internal temperature of 20 to 30° C. over 1 hour or more, and aged and stirred at the same temperature for 1 hour or more. EtOAc (4350 L) was added dropwise thereto at an internal temperature of 20 to 30° C. for 1 hour or more, followed by aging and stirring at the same temperature overnight. The precipitated crystals were filtered. The wet crystals were washed with an EtOH/EtOAc (145 L/290 L) solution. The wet crystals were dried at an external temperature of 40° C. overnight under reduced pressure to obtain a crystal (Form B45, 161 kg) of 4-{[(1R,2s,3S, 5s,7s)-5-hydroxy-2-adamantyl]amino}-1H-pyrrolo[2,3-b]pyridine-5-carboxamide hydrobromide.

(Alternative Method for Preparing Form B45 Crystal of Hydrobromide)

(In Case of not Adding Seed Crystal)

A reaction vessel was sufficiently dried and purged with nitrogen, and water (585 L) was added thereto. Subsequently, 4-{[(1R,2s,3S,5s,7s)-5-hydroxy-2-adamantyl]amino}-1H-pyrrolo[2,3-b]pyridine-5-carboxamide (225 kg) and EtOH (2250 L) were added thereto, followed by starting stirring. The internal temperature was adjusted to 25° C., 48% hydrobromic acid (127.8 kg) was added thereto at the same temperature, and the container and the vessel wall were washed with EtOH (90 L). After completion of the addition of materials, the dissolution of the reaction mixture was confirmed and the pH was measured to ensure that it was in the range of 1.5 to 1.9. If the pH was outside the range, it was adjusted to a predetermined pH using 48% hydrobromic acid (hydrobromic acid 48%: about 11.6 kg). After raising the temperature to an internal temperature of 70° C., and then confirming the dissolution, the mixture was stirred for 5 minutes or more. The solution was clarified and filtered while maintaining the internal temperature at 60° C. or higher, and the filter was washed with warm EtOH (450 L) which had been warmed to 50° C. in advance by passing it through a dissolution vessel. The clarified filtrate was gradually cooled to an internal temperature of 45° C., and EtOAc (6750 L) which had been passed through the filter at an internal temperature of 45° C. was added dropwise over 6 hours. After completion of dropwise addition, the mixture was stirred at an internal temperature of 45° C. for 10 hours or more. Subsequently, the mixture was cooled to an internal temperature of 25° C. using a follow-up temperature-controlled cooler, and stirred for 3 hours at an internal temperature of 25° C. A predetermined concentration of the supernatant and the crystal form of the precipitated crystals were confirmed, and filtered. A mixed solvent of EtOH/EtOAc in the (225 L/450 L) was prepared, and the cake was washed with the mixed solvent. The obtained wet crystals were dried at an external temperature of 40° C. for 10 hours or more under reduced pressure to obtain a crystal (Form B45, 250 kg) of 4-{[(1R,2s,3S,5s,7s)-5-hydroxy-2-adamantyl]amino}-1H-pyrrolo[2,3-b]pyridine-5-carboxamide hydrobromide.

$^1$H-NMR (600 MHz, d$_6$-DMSO) δ: 1.49 (2H, m), 1.68 (2H, m), 1.71 (2H, m), 1.80 (2H, m), 1.91 (2H, m), 2.10 (1H, m), 2.20 (2H, m), 3.70-4.00 (1H, brs), 4.28 (1H, m), 6.66 (1H, m), 7.39 (1H, m), 7.75 (1H, brs), 8.38 (1H, brs), 8.55 (1H, s), 11.17 (1H, d, 7.8 Hz), 12.5 (1H, brs), 14.17 (1H, brs)

Elemental analysis: theoretical values: C, 53.08%, H, 5.69%, N, 13.76%, O 7.86%, Br 19.62%;

Found values: C, 53.02%, H, 5.74%, N, 13.73%, Br 19.42%.

Molecular composition: $C_{18}H_{22}N_4O_2 \cdot HBr$

MS: 327.0 (M+H)$^+$

From the results of the elemental analysis, 4-{[(1R,2s,3S,5s,7s)-5-hydroxy-2-adamantyl]amino}-1H-pyrrolo[2,3-b]pyridine-5-carboxamide hydrobromide was monohydrobromide.

Example 2

Form A87 Crystal of Hydrobromide

4-{[(1R,2s,3S,5s,7s)-5-Hydroxy-2-adamantyl]amino}-1H-pyrrolo[2,3-b]pyridine-5-carboxamide (6.0 g) was put into EtOH/water (57.6 mL/14.4 mL). At 50 to 60° C., 48% hydrobromic acid was added thereto, followed by stirring for 15 minutes or more and washing with EtOH (18 mL). EtOAc (180 mL) was added dropwise thereto at 45° C. to 55° C. over 30 minutes. After stirring at 15° C. to 25° C., crystals were precipitated. The crystals were collected by filtration and washed with a mixed solvent of EtOH/EtOAc (6 mL/12 mL). The crystals were dried in vacuo to obtain a seed crystal (Form A87, 6.11 g) of 4-{[(1R,2s,3S,5s,7s)-5-hydroxy-2-adamantyl]amino}-1H-pyrrolo[2,3-b]pyridine-5-carboxamide hydrobromide.

4-{[(1R,2s,3S,5s,7s)-5-hydroxy-2-adamantyl]amino}-1H-pyrrolo[2,3-b]pyridine-5-carboxamide (3.0 g), EtOH (24 mL), water (6 mL), and 48% hydrobromic acid (1.55 g) were sequentially added at room temperature. After adding the components, the mixture was warmed to an internal temperature of 60° C. or higher, and stirred. After confirming the completion of dissolution, the dissolution liquid was clarified and filtered at an internal temperature of 60° C. or higher, and washed with warm EtOH (9 mL). At an internal temperature of 70° C. or higher, EtOH (21 mL) was added dropwise thereto, and seed crystals (Form A87, 30 mg) of 4-{[(1R,2s,3S,5s,7s)-5-hydroxy-2-adamantyl]amino}-1H-pyrrolo[2,3-b]pyridine-5-carboxamide hydrobromide were added thereto at an internal temperature of 70° C., followed by aging and stirring at an internal temperature of 65 to 70° C. overnight. The mixture was subsequently cooled to an internal temperature of 20 to 30° C. over 1 hour or more, and aged and stirred at the same temperature overnight. EtOAc (90 mL) was added dropwise thereto at an internal temperature of 20 to 30° C., followed by aging and stirring at the same temperature for 1 hour or more. The precipitated crystals were collected by filtration. The wet crystals were washed with an EtOH/EtOAc (3 mL/12 mL) solution. The wet crystals were dried under reduced pressure overnight to obtain a crystal (Form A87, 3.09 g) of 4-{[(1R,2s,3S,5s,7s)-5-hydroxy-2-adamantyl]amino}-1H-pyrrolo[2,3-b]pyridine-5-carboxamide hydrobromide.

Example 3

Form A61 Crystal of Hydrobromide

4-{[(1R,2s,3S,5s,7s)-5-Hydroxy-2-adamantyl]amino}-1H-pyrrolo[2,3-b]pyridine-5-carboxamide (5.0 g), EtOH (48 mL), water (12 mL), and 48% hydrobromic acid (2.58 g) were sequentially placed at room temperature. After placing the components, the mixture was warmed to an internal temperature of 70° C., and stirred. After confirming the completion of dissolution, the dissolution liquid was clarified and filtered at an internal temperature of 70° C., and washed with warm EtOH (15 mL). The mixture was cooled to an internal temperature of 50 to 60° C., and EtOAc (150 mL) was added dropwise thereto at the same temperature for 1 hour or more. After completion of dropwise addition, the mixture was gradually cooled to 20 to 30° C., and aged and stirred at the same temperature for 1 hour or more. The precipitated crystals were collected by filtration. The wet crystals were washed with an EtOH/EtOAc (5 mL/10 mL) solution. The wet crystals were dried under reduced pressure overnight to obtain a crystal (Form A61, 5.19 g) of 4-{[(1R,2s,3S,5s,7s)-5-hydroxy-2-adamantyl]amino}-1H-pyrrolo[2,3-b]pyridine-5-carboxamide hydrobromide.

Example 4

Form A36 Crystal of Hydrobromide

To a suspension of 4-{[(1R,2s,3S,5s,7s)-5-hydroxy-2-adamantyl]amino}-1H-pyrrolo[2,3-b]pyridine-5-carboxamide (500 mg) in EtOAc was added 48% hydrobromic acid (258 μL), followed by heating, refluxing, and stirring for 1 hour, and then leaving to be cooled to room temperature. The precipitated crystals were collected by filtration and washed with EtOAc. The obtained crystals were subjected to reduced pressure and dried at 60° C. to obtain a crystal (Form A36, 625 mg) of 4-{[(1R,2s,3S,5s,7s)-5-hydroxy-2-adamantyl]amino}-1H-pyrrolo[2,3-b]pyridine-5-carboxamide monohydrobromide.

Example 5

Form B11 Crystal of Hydrobromide Monohydrate

4-{[(1R,2s,3S,5s,7s)-5-hydroxy-2-adamantyl]amino}-1H-pyrrolo[2,3-b]pyridine-5-carboxamide (5.0 g), EtOH (48 mL), water (12 mL), and 48% hydrobromic acid (2.58 g) were sequentially placed at room temperature. After placing the components, the mixture was warmed to an internal temperature 70° C. or higher, and stirred. After confirming that the components were completely dissolved therein, the dissolution liquid was clarified and filtered at an internal temperature of 70° C. or higher, and washed with warm EtOH (15 mL). At an internal temperature of about 35° C., seed crystals (Form A87, 49.0 mg) of 4-{[(1R,2s,3S,5s,7s)-5-hydroxy-2-adamantyl]amino}-1H-pyrrolo[2,3-b]pyridine-5-carboxamide hydrobromide were added thereto, followed by aging and stirring at an internal temperature of 30 to 40° C. for 4 hours. Subsequently, the mixture was cooled to an internal temperature of 20 to 30° C., and aged and stirred at the same temperature overnight. At an internal temperature of 20 to 25° C., EtOAc (150 mL) was added dropwise thereto for 1 hour or more, followed by aging and stirring at the same temperature for 30 minutes or more. The precipitated crystals were collected by filtration. The wet crystals were washed with an EtOH/EtOAc (5 mL/10 mL) solution. The wet crystals were dried overnight under reduced pressure to obtain a crystal (Form B11, 5.24 g) of 4-{[(1R,2s,3S,5s,7s)-5-hydroxy-2-adamantyl]amino}-1H-pyrrolo[2,3-b]pyridine-5-carboxamide hydrobromide monohydrate.

Example 6

Form B21 Crystal of Hydrobromide Dihydrate

4-{[(1R,2s,3S,5s,7s)-5-hydroxy-2-adamantyl]amino}-1H-pyrrolo[2,3-b]pyridine-5-carboxamide (5.0 g), EtOH (18 mL), water (12 mL), and 48% hydrobromic acid (2.58 g) were sequentially placed at room temperature. After placing the components, the mixture was warmed to an internal temperature 60° C. or higher, and stirred. After confirming that the components were completely dissolved therein, the dissolution liquid was clarified and filtered at an internal temperature of 60° C. or higher, and washed with warm EtOH (10 mL). The mixture was cooled to an internal temperature of about 45 to 50° C., and aged and stirred for 2 hours. Subsequently, the mixture was cooled to an internal temperature of 20 to 30° C., and aged and stirred at the same temperature overnight. At an internal temperature of 20 to 30° C., EtOAc (160 mL) was added dropwise thereto for 1 hour or more, followed by aging and stirring at the same temperature for 1 hour or more. The precipitated crystals were filtered. The wet crystals were washed with an EtOH/EtOAc (3 mL/12 mL) solution. The wet crystals were dried overnight under reduced pressure to obtain a crystal (Form B21, 6.05 g) of 4-{[(1R,2s,3S,5s,7s)-5-hydroxy-2-adamantyl]amino}-1H-pyrrolo[2,3-b]pyridine-5-carboxamide hydrobromide dihydrate.

Example 7

Tautomerism of Each Crystal

Example 7-1

(Crystal Form Conversion; Hydrobromide Form B21→Form A61)
4-{[(1R,2s,3S,5s,7s)-5-hydroxy-2-adamantyl]amino}-1H-pyrrolo[2,3-b]pyridine-5-carboxamide hydrobromide dihydrate (Form B21, 300 mg) and EtOH (3 mL) were sequentially placed at room temperature, and suspended overnight. After suspending, the crystals were collected by filtration at room temperature and the wet crystals were washed with EtOH. The wet crystals were dried overnight under reduced pressure to obtain a crystal (Form A61, 258 mg) of 4-{[(1R,2s,3S,5s,7s)-5-hydroxy-2-adamantyl]amino}-1H-pyrrolo[2,3-b]pyridine-5-carboxamide hydrobromide.

Example 7-2

Crystal Form Conversion; Hydrobromide Form B11→Form B21

4-{[(1R,2s,3S,5s,7s)-5-hydroxy-2-adamantyl]amino}-1H-pyrrolo[2,3-b]pyridine-5-carboxamide hydrobromide monohydrate (Form B11, 2.0 g), EtOH (7 mL), and water (3 mL) were sequentially placed at room temperature, and suspended overnight. After suspending, the crystals were collected by filtration at room temperature and the wet crystals were washed with a 70% aqueous EtOH solution. The wet crystals were dried overnight under reduced pressure to obtain a crystal (Form B21, 1.54 g) of 4-{[(1R,2s,3S,5s,7s)-5-hydroxy-2-adamantyl]amino}-1H-pyrrolo[2,3-b]pyridine-5-carboxamide hydrobromide dihydrate.

Example 7-3

Crystal Form Conversion; Hydrobromide Form A61→Form B21

4-{[(1R,2s,3S,5s,7s)-5-hydroxy-2-adamantyl]amino}-1H-pyrrolo[2,3-b]pyridine-5-carboxamide hydrobromide (Form A61, 1.0 g), EtOH (3.5 mL), and water (1.5 mL) were sequentially placed at room temperature and suspended overnight. After suspending, the crystals were collected by filtration at room temperature and the wet crystals were washed with a 70% aqueous EtOH solution. The wet crystals were dried overnight under reduced pressure to obtain a crystal (Form B21, 827 mg) of 4-{[(1R,2s,3S,5s,7s)-5-hydroxy-2-adamantyl]amino}-1H-pyrrolo[2,3-b]pyridine-5-carboxamide hydrobromide dihydrate.

Reference Example 1

Preparation Example of Monohydrate Crystal of Free Form of Compound (I)

Under a nitrogen atmosphere, in 4-chloro-1H-pyrrolo[2,3-b]pyridine-5-carboxamide (44.5 g), (1s,3R,4s,5S)-4-aminoadamantan-1-ol (57.0 g) and tributylamine (162.6 mL) were put into NMP (222.5 mL), followed by heating and stirring at a bath temperature of 200° C. for 2.5 hours. The reaction solution was left to be cooled, and then added dropwise to water/Et$_2$O (6 L/0.5 L) under stirring, followed by stirring for 30 minutes. The obtained solid was collected by filtration, washed with water (400 mL) twice and with Et$_2$O (300 mL) twice, and then dried. The obtained solid was warmed and dissolved in MeOH (1.8 L), and filtered while warming. The obtained mother liquid was concentrated under reduced pressure, and to the residue was added MeOH (1.8 L), followed by heating and dissolving. The obtained solution was left to be cooled, then stirred at room temperature, and aged overnight. The precipitated solid was collected by filtration, washed with EtOH, and dried under reduced pressure. The obtained solid was suspended in EtOH (250 mL), followed by stirring at room temperature for 1 hour. The solid was collected by filtration, washed with EtOH, and then dried under reduced pressure. The obtained solid was suspended in water (900 mL), and stirred at a bath temperature of 70° C. for 2 hours. The solid was collected by filtration, washed with water, and then dried under reduced pressure. The solid was suspended in water (900 mL) and stirred at a bath temperature 70° C. for 2 hours. The solid was collected by filtration, washed with water, and dried under reduced pressure to obtain a crystal (Form A01, 44 g) of 4-{[(1R,2s,3S,5s,7s)-5-hydroxy-2-adamantyl]amino}-1H-pyrrolo[2,3-b]pyridine-5-carboxamide monohydrate.

Test Example 1

Stability Test

A sample was stored with light-shielding under the condition of 70° C., 70° C.·75% RH for 2 weeks. The total amount of the related substance after storage was measured using HPLC, and the change in crystal forms was measured by means of powder X-ray diffraction. Further, in Comparative Examples, using the starting material that had been stored under cooling for 2 weeks as an initial, the test on the total amount of the related substance and the powder X-ray diffraction were performed.

(Conditions for Storage of Samples)

The test drug was stored under the following conditions.

diameter 3 μm, 2.1 mm×100 mm), column temperature: 40° C. (column thermostat vessel was used), mobile phase: Liquid A—1000 mL of water was added to perchlorate buffer at pH 2.5 {sodium perchlorate (NaClO$_4$.H$_2$O) (1.40 g) for dissolution, and adjusted to a pH of 2.5 with diluted perchloric acid (dilution of 100 mL of a commercially available 60% perchloric acid solution with 1900 mL of water)}. Liquid B—MeCN for LC, flow rate: 0.2 mL/min, Injection amount: 1 μL, (gradient setting: Liquid B 10% at 0.0 minutes to Liquid B 90% at 35 minutes).

Powder X-ray diffraction; tube: Cu, tube current: 300 mA, tube voltage, 50 kV, sampling width: 0.02°, scan speed: 4°/min, wavelength: 1.54056 angstroms, measured diffraction angle range (2θ): 2.5 to 40°

(Results)

The results of the stability test of various crystal forms are shown in Table 1. In the table below, LC represents the results of measuring the total amount of the related materials using HPLC. % represents the proportion of the total amount of the related materials. XRD represents the change in the crystal forms when stored at 70° C. and 70° C.·75% RH.

TABLE 1

| | | Crystal form | | | | | |
| --- | --- | --- | --- | --- | --- | --- | --- |
| | | Form B45 | Form A87 | Form A61 | Form A36 | Form B11 | Form B21 |
| Initial | LC | 0.11% | 1.60% | 0.44% | 0.43% | 0.43% | 0.00% |
| 70° C. 2 weeks | LC XRD | 0.11% No change | 1.64% No change | 0.44% No change | 0.34% No change | 0.43% No change | 0.05% Transition to Form A61 (Form A87 was also present) |
| 70° C. 75% RH 2 weeks | LC XRD | 0.11% No change | 1.51% No change | 0.43% No change | 0.28% Transition to Form A87 + A61 | 0.43% No change | 0.05% Transition to Form A87 |
| Xe lamp 40H | LC XRD | 0.11% No change | 1.32% No change | 0.77% — | 0.76% — | 0.48% No change | 0.05% No change |
| Note | | | Colored with light. Changed. | Colored with light. Changed. | Transition under warming | Transited to Form A61 after dehydration | Transited to anhydride at 70° C. |

Initial (Stored under the cooling conditions): About 5 mg was collected with a 10 mL centrifuge tube and stored in a refrigerator.

70° C. (stored at 70° C.): About 5 mg was collected with a 10 mL centrifuge tube and stored in a mini-jet oven at 70° C. for 14 days.

70° C.·75% RH (stored at 70° C. and 75% relative humidity): About 5 mg was collected with a 10 mL centrifuge tube, a sample was put into a desiccator at 75% relative humidity in the open state, and the desiccator was stored in a mini jet oven at 70° C. for 14 days.

Xe lamp: This product was placed in a plastic Petri dish and stored for 40 hours under a Xe lamp (25° C. RH 60%, total irradiance 1,200,000 lx·h, total near-ultraviolet radiation energy 200 W·h/m$^2$ or more).

(Preparation of Sample Solution for HPLC)

Initial, a product stored at 70° C. and a product stored at 70° C. and 75% RH were dissolved in a mixed solution (1:1) of MeCN for LC/water to exactly 10 mL, which was used as a sample solution.

HPLC; Detector: ultraviolet absorptiometer (wavelength measurement; 254 nm), column: Inertsil ODS-3 (particle As seen from Table 1, the crystals of hydrobromide of the present invention have no change in the purity and are chemically stable even when stored at 70° C. or 70° C.·75% RH for 2 weeks. Further, the crystals of B45, A87 and A61 are physically stable and were not found to have a change in the crystal forms.

The hydrate crystals of the free from obtained in Reference Example 1 above were stored under the conditions of no humidity at 70° C., and they were thus underwent transition to an anhydride in a free form. Further, the anhydride in a free form changed to hydrate with humidity at 70° C. Therefore, it was demonstrated that the free form is not stable with respect to temperature and humidity even when crystallized.

Test Example 2

Solubility Test

In a glass test tube, 4-{[(1R,2s,3S,5s,7s)-5-hydroxy-2-adamantyl]amino}-1H-pyrrolo[2,3-b]pyridine-5-carboxamide hydrobromide was added to a 84% aqueous EtOH solution in the state where the residues after dissolution were generated, followed by stirring at each temperature for 30 minutes or more. After stirring, the supernatant was filtered and the concentration of the filtrate was quantified by means of HPLC.

(Analysis Conditions)

HPLC; Columns to be charged: Unison UK Phenyl (manufactured by Imtakt Corporation), particle diameter 3 µm, 4.6 mm×250 mm Mobile phase: perchlorate buffer at pH 2.5 (0.01 mol/L) $^{(note)}$/mixed solution with MeCN for LC (4:1), (note) perchlorate buffer at pH 2.5 (0.01 mol/L): 1.40 g of sodium perchlorate ($NaClO_4.H_2O$, JIS reagent, special grade) was dissolved in 1000 mL of water, and adjusted to pH 2.5 with dilute perchloric acid (dilution of 100 mL of a commercially available 60% perchloric acid solution with 1900 mL of water). Flow rate of mobile phase: about 1.0 mL/min. Detector: ultraviolet absorptiometer (wavelength for measurement: 235 nm), column temperature: 50° C. (column thermostat vessel was used)

(Results)

As seen from Table 2, each crystal had a solubility of 20 g/L or more at all temperature. Among them, the lowest solubility crystal form was a Form B45 crystal. Typically, it is known that crystals having a lower solubility than other crystals are thermodynamically stable, and it was demonstrated that the Form B45 crystal is more stable thermodynamically than other crystal forms (Table 2, FIG. 1).

TABLE 2

| | | Crystal form | | | | |
|---|---|---|---|---|---|---|
| | | Form B45 | Form A87 | Form A61 | Form B11 | Form B21 |
| Temperature | 25° C. | 23.7 g/L | 36.8 g/L | 37.2 g/L | 35.0 g/L | 36.1 g/L |
| | 35° C. | 29.4 g/L | 46.0 g/L | 45.5 g/L | 44.1 g/L | 46.3 g/L |
| | 50° C. | 36.7 g/L | 48.9 g/L | 53.8 g/L | 60.1 g/L | 58.2 g/L |

Test Example 3

Transition of Crystal Forms and Supernatant Concentrations During Solvent-Mediated Transition The Form A61 crystals were stirred at room temperature and transition of crystal forms was attempted in a 84% EtOH solution. As a result, the Form A61 crystal underwent transition to a Form B45 after 4 hours. Accordingly, it was proved that the Form A61 underwent transition to a Form B45. In the solvent-meditated transition, it was demonstrated that the crystals undergo transition to stable crystal forms over time, and thus, the Form B45 is more stable.

Example 8

Succinate Form A24 Crystal

4-{[(1R,2s,3S,5s,7s)-5-Hydroxy-2-adamantyl]amino}-1H-pyrrolo[2,3-b]pyridine-5-carboxamide (500 mg) was put into MeOH (25 mL), and a succinic acid solution {formed by dissolving 15.3 mL of succinic acid (0.59 g) in MeOH (50 mL)} was added thereto. The reaction mixture was heated and stirred in a warm bath of 80° C. for 1 hour, then concentrated under reduced pressure, and dried at 60° C. in vacuo. 0.15 g of the obtained residue was weighed and used, and it was heated and stirred with MEK (12 mL) in a warm bath at 80° C. for 1 hour, and left to be cooled. The solid was collected by filtration and washed with MEK. The residue was dried at 60° C. in vacuo to obtain a crystal (Form A24, 110 mg) of 4-{[(1R,2s,3S,5s,7s)-5-hydroxy-2-adamantyl]amino}-1H-pyrrolo[2,3-b]pyridine-5-carboxamide succinate.

Example 9

Form A33 Crystals of Hydrochloride Anhydride

4-{[(1R,2s,3S,5s,7s)-5-Hydroxy-2-adamantyl]amino}-1H-pyrrolo[2,3-b]pyridine-5-carboxamide (500 mg) was put into EtOAc (25 mL), and 4M HCl/EtOAc (383 µL) was added thereto, followed by heating and refluxing in a warm bath at 80° C. for 1 hour, and then leaving to be cooled and stirring. The obtained solid was collected by filtration, washed with EtOAc, and dried under the conditions of 60° C. and vacuum to obtain a crystal (Form A33, 398 mg) of 4-{[(1R,2s,3S,5s,7s)-5-hydroxy-2-adamantyl]amino}-1H-pyrrolo[2,3-b]pyridine-5-carboxamide monohydrochloride.

Example 10

Form A34 Crystals of Hydrochloride Hydrate

To a suspension of 4-{[(1R,2s,3S,5s,7s)-5-hydroxy-2-adamantyl]amino}-1H-pyrrolo[2,3-b]pyridine-5-carboxamide (500 mg) in EtOAc was added a 4M hydrochloric acid/ethyl acetate solution (383 µL), followed by heating and refluxing for 1 hour, and then leaving to be cooled to room temperature and stirring. The precipitated solid was collected by filtration and washed with EtOAc. The obtained solid was dried at 60° C. under reduced pressure to obtain a solid of 4-{[(1R,2s,3S,5s,7s)-5-hydroxy-2-adamantyl]amino}-1H-pyrrolo[2,3-b] pyridine-5-carboxamide monohydrochloride (398 mg). To the obtained suspension of 4-{[(1R,2s,3S,5s,7s)-5-hydroxy-2-adamantyl]amino}-1H-pyrrolo[2,3-b]pyridine-5-carboxamide monohydrochloride (100 mg) in EtOH (2.0 mL) was added water (300 µL), followed by heating and refluxing with refluxing, and then leaving to be cooled to room temperature with stirring. The precipitated solid was collected by filtration and washed with 90% EtOAc/water. The obtained crystals were dried at 60° C. under reduced pressure to obtain 4-{[(1R,2s,3S,5s,7s)-5-hydroxy-2-adamantyl]amino}-1H-pyrrolo[2,3-b]pyridine-5-carboxamide monohydrochloride hydrate (Form A34, 20 mg).

Test Example 4

Stability Test

In a similar manner as in Test Example 1, stability tests were performed with the crystals obtained in Examples 8 to 10. The results are shown in Tables below.

TABLE 3

| Crystal Form | Succinate Form A24 | Hydrochloride (anhydride) Form A33 | Hydrochloride (hydrate) Form A34 |
|---|---|---|---|
| Initial | LC 0.25% | 0.49% | 0.10% |
| 70° C. 2 W | LC 0.19% | 0.48% | 0.10% |
| 70° C. 75% RH 2 W | LC 0.25% | 0.48% (transited to Form A52) | 0.10% |
| Xe lump 40H | LC 0.19% | 0.79% | 0.30% |
| Note | Chemically stable | Substantially chemically stable | Substantially chemically stable |

Test Example 5

The solubility was measured with a 80% aqueous EtOH solution. The results are shown in Tables below. Further, the crystals of 0.5 L-tartrate and lactate were prepared as crystallized from a crystallization solvent described in Tables below.

TABLE 4

| Salt | Crystal | Crystallization solvent | Solubility (mg/mL) |
|---|---|---|---|
| Hydrochloric acid | Anhydride (Form A33) | EtOAc or MeOH | 25 to 50 |
| Hydrochloric acid | Hydrate (Form A34) | EtOH/$H_2O$ or acetone/$H_2O$ | 16.7 to 25 |
| Succinic acid | Anhydride (Form A24) | MEK | 20 to 25 |
| Free form | Hydrate (Form A01) | MeOH/EtOH/$H_2O$ | <10 |
| 0.5 L-tartaric acid | Hydrate (Form A26) | EtOH/$H_2O$ | <10 |
| 0.5 L-tartaric acid | Anhydride (Form A25) | MeOH | <10 |
| Sulfuric acid | Anhydride (Form A38) | MeOH | <10 |

4-{[(1R,2s,3S,5s,7s)-5-Hydroxy-2-adamantyl]amino}-1H-pyrrolo[2,3-b]pyridine-5-carboxamide succinate, 4-{[(1R,2s,3S,5s,7s)-5-hydroxy-2-adamantyl]amino}-1H-pyrrolo[2,3-b]pyridine-5-carboxamide hydrobromide, and 4-{[(1R,2s,3S,5s,7s)-5-hydroxy-2-adamantyl]amino}-1H-pyrrolo[2,3-b]pyridine-5-carboxamide hydrochloride and crystals thereof of the present invention have solubility suitable for a solvent for a solid dispersion, and are useful as a bulk material for the preparation of a solid preparation, in particular, a solid dispersion preparation.

Furthermore, the crystal of 4-{[(1R,2s,3S,5s,7s)-5-hydroxy-2-adamantyl]amino}-1H-pyrrolo[2,3-b]pyridine-5-carboxamide hydrobromide of the present invention has excellent stability in a solid state, and in particular, the Form B45 crystal is useful as a bulk material for the preparation of a pharmaceutical product.

The invention claimed is:

1. A crystal of 4-{[(1R,2s,3S,5s,7s)-5-hydroxy-2-adamantyl]amino}-1H-pyrrolo[2,3-b]pyridine-5-carboxamide hydrobromide, having characteristic peaks at angles 2θ (°) of about 9.0, 17.6, 18.1, 18.3, 23.0, and 27.3 in powder X-ray diffraction.

2. The crystal according to claim 1, wherein a starting melting temperature is around 315° C.

3. A crystal of 4-{[(1R,2s,3S,5s,7s)-5-hydroxy-2-adamantyl]amino}-1H-pyrrolo[2,3-b]pyridine-5-carboxamide hydrobromide, having characteristic peaks at angles 2θ (°) of about 8.3, 13.4, 18.3, 19.3, 20.8, 25.1, and 28.6 in powder X-ray diffraction.

4. A crystal of 4-{[(1R,2s,3S,5s,7s)-5-hydroxy-2-adamantyl]amino}-1H-pyrrolo[2,3-b]pyridine-5-carboxamide hydrobromide, having characteristic peaks at angles 2θ (°) of about 7.3, 13.8, 16.8, 18.4, 20.9, and 21.9 in powder X-ray diffraction.

5. A crystal of 4-{[(1R,2s,3S,5s,7s)-5-hydroxy-2-adamantyl]amino}-1H-pyrrolo[2,3-b]pyridine-5-carboxamide hydrobromide, having characteristic peaks at angles 2θ (°) of about 8.9, 16.6, 17.9, 18.7, 21.3, and 23.8 in powder X-ray diffraction.

6. A crystal of 4-{[(1R,2s,3S,5s,7s)-5-hydroxy-2-adamantyl]amino}-1H-pyrrolo[2,3-b]pyridine-5-carboxamide hydrobromide, having characteristic peaks at angles 2θ (°) of about 7.8, 12.8, 16.4, 17.1, 18.3, 24.7, 25.3, and 25.8 in powder X-ray diffraction.

7. A crystal of 4-{[(1R,2s,3S,5s,7s)-5-hydroxy-2-adamantyl]amino}-1H-pyrrolo[2,3-b]pyridine-5-carboxamide hydrobromide, having characteristic peaks at angles 2θ (°) of about 15.7, 17.5, 19.5, 20.5, 23.0, 23.7, and 27.0 in powder X-ray diffraction.

* * * * *